United States Patent
Deb et al.

(10) Patent No.: US 12,281,070 B2
(45) Date of Patent: Apr. 22, 2025

(54) WATER SOLUBLE ANTIVIRAL AND ANTIMICROBIAL COMPOUND AND PROCESS FOR PREPARATION THEREOF

(71) Applicants: Nilanjan Deb, Kolkata (IN); Mukesh Agarwal, Kolkata (IN)

(72) Inventors: Nilanjan Deb, Kolkata (IN); Mukesh Agarwal, Kolkata (IN)

( * ) Notice: Subject to any disclaimer, the term of this patent is extended or adjusted under 35 U.S.C. 154(b) by 117 days.

(21) Appl. No.: 17/907,253

(22) PCT Filed: May 10, 2021

(86) PCT No.: PCT/IB2021/053948
§ 371 (c)(1),
(2) Date: Sep. 23, 2022

(87) PCT Pub. No.: WO2022/106908
PCT Pub. Date: May 27, 2022

(65) Prior Publication Data
US 2023/0121754 A1    Apr. 20, 2023

(30) Foreign Application Priority Data

Nov. 23, 2020  (IN) .............................. 202031050892
Mar. 3, 2021   (IN) .............................. 202131008965

(51) Int. Cl.
C07C 69/30   (2006.01)
C07C 69/16   (2006.01)

(52) U.S. Cl.
CPC .............. *C07C 69/30* (2013.01); *C07C 69/16* (2013.01)

(58) Field of Classification Search
CPC .......... C07C 69/30; C07C 69/16; C07C 69/58
(Continued)

(56) References Cited

U.S. PATENT DOCUMENTS

| 7,964,640 B2 * | 6/2011 | Wolf ....................... A61P 43/00 514/557 |
| 2003/0194412 A1 * | 10/2003 | Baker .................... A01N 25/04 424/769 |
| 2021/0379091 A1 * | 12/2021 | Savage ..................... A01P 1/00 |

FOREIGN PATENT DOCUMENTS

WO    WO 1990011096 A1    10/1990

OTHER PUBLICATIONS

International Search Report, dated Aug. 25, 2021 for corresponding International Application No. PCT/IB2021/053948 (3 pages).
(Continued)

*Primary Examiner* — Ellen M McAvoy
(74) *Attorney, Agent, or Firm* — Intellectual Property Law Group LLP

(57) ABSTRACT

The present invention discloses compound of Formula A represented by the structure Formula A

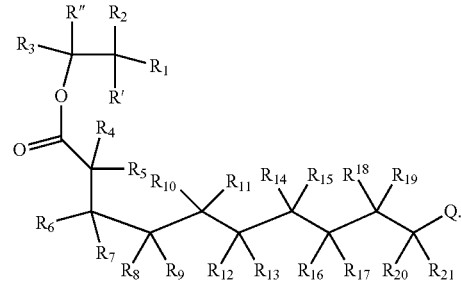

24 Claims, 26 Drawing Sheets
(22 of 26 Drawing Sheet(s) Filed in Color)

(58) Field of Classification Search
USPC .......................................................... 508/463
See application file for complete search history.

(56) References Cited

OTHER PUBLICATIONS

Written Opinion of ISA, dated Aug. 25, 2021 for corresponding International Application No. PCT/IB2021/053948 (6 pages).
Emin Yilmaz et al., "Comparison of the Glycerol Monostearate and Polyglycerol Stearate Oleogels: Effects of Amphiphile Addition", Apr. 28, 2020, https://d197for5662m48.cloudfront.net/documents/publicationstatus/34304/preprint_pdf/11f2aac11f8fb688def8f9d7402cfd87.pdf (12 pages).
Lisa Elmen et al., "Dietary Emulsifier Sodium Stearoyl Lactylate Alters Gut Microbiota in vitro and Inhibits Bacterial Butyrate Producers". Frontiers in Microbiology, vol. 11, May 2020, DOI: 10.3389/fmicb.2020.00892 (14 pages).

* cited by examiner

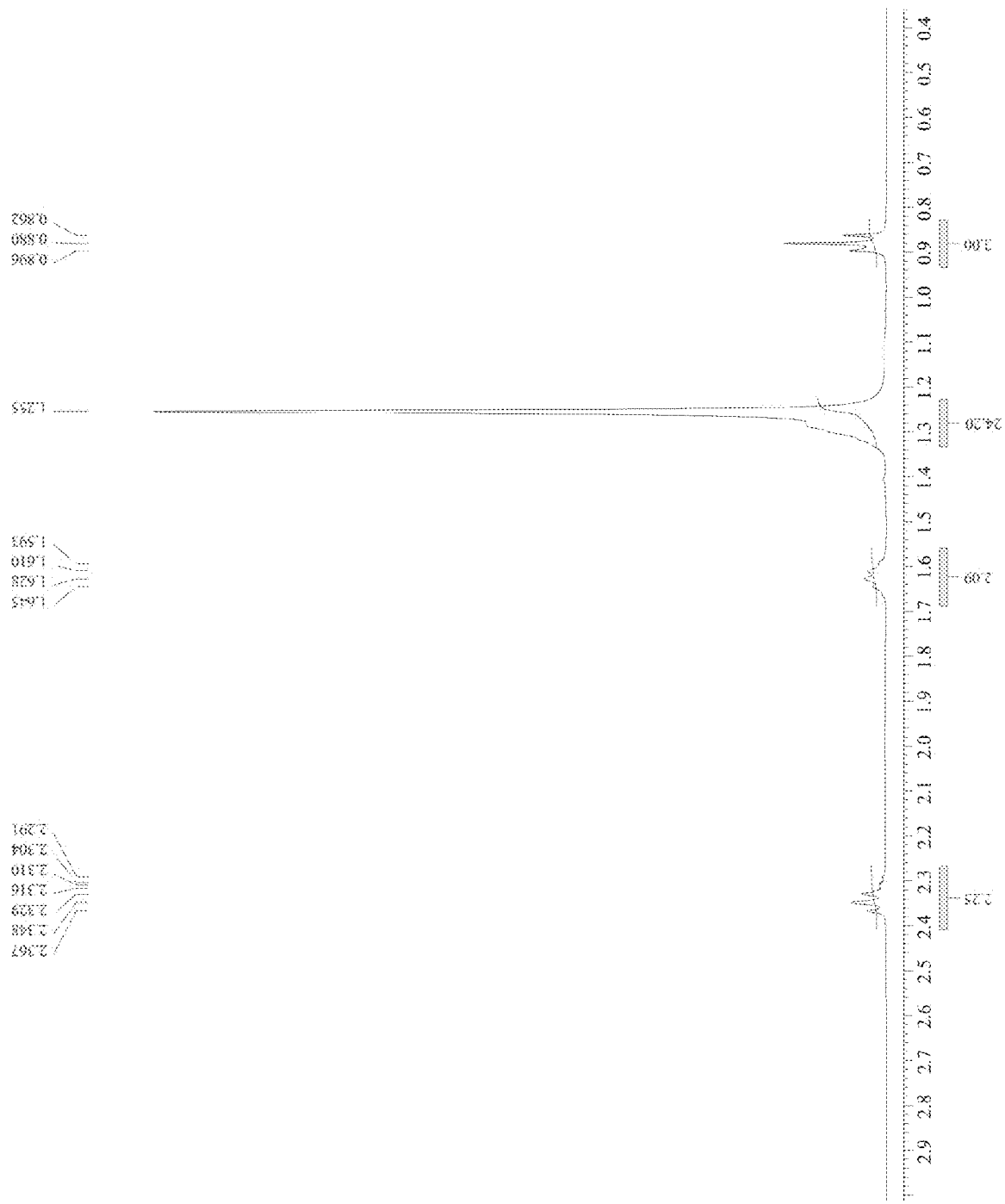

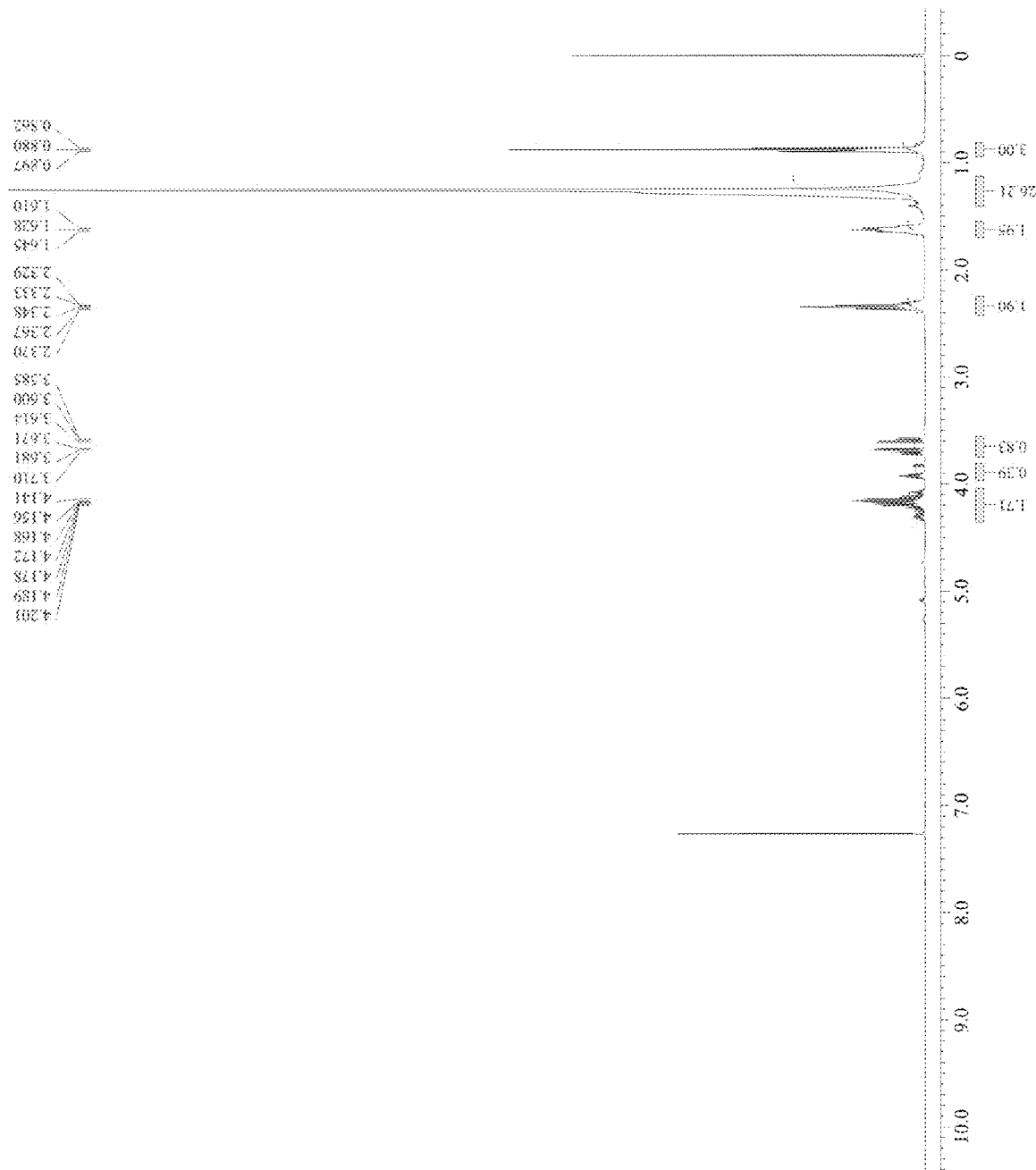

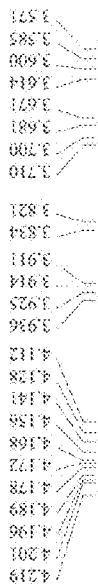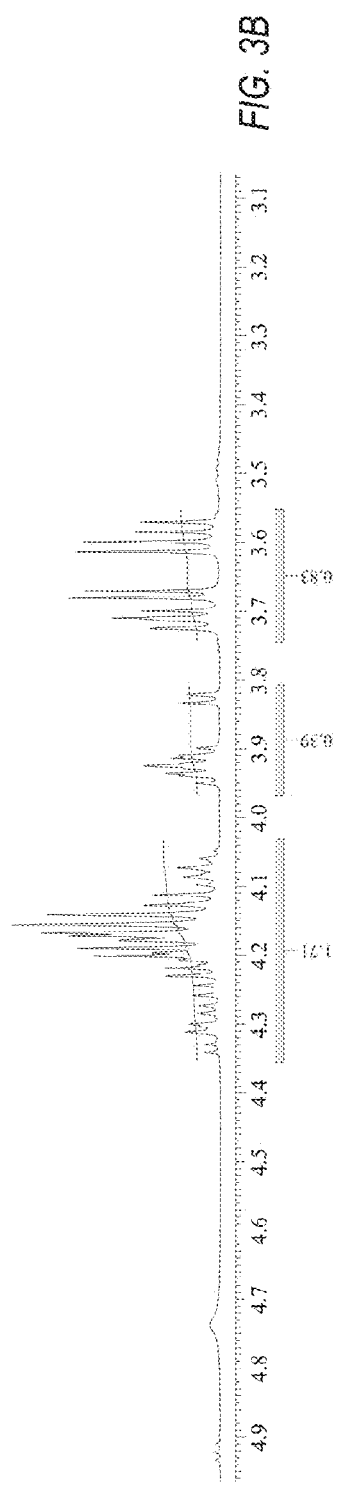
FIG. 3B

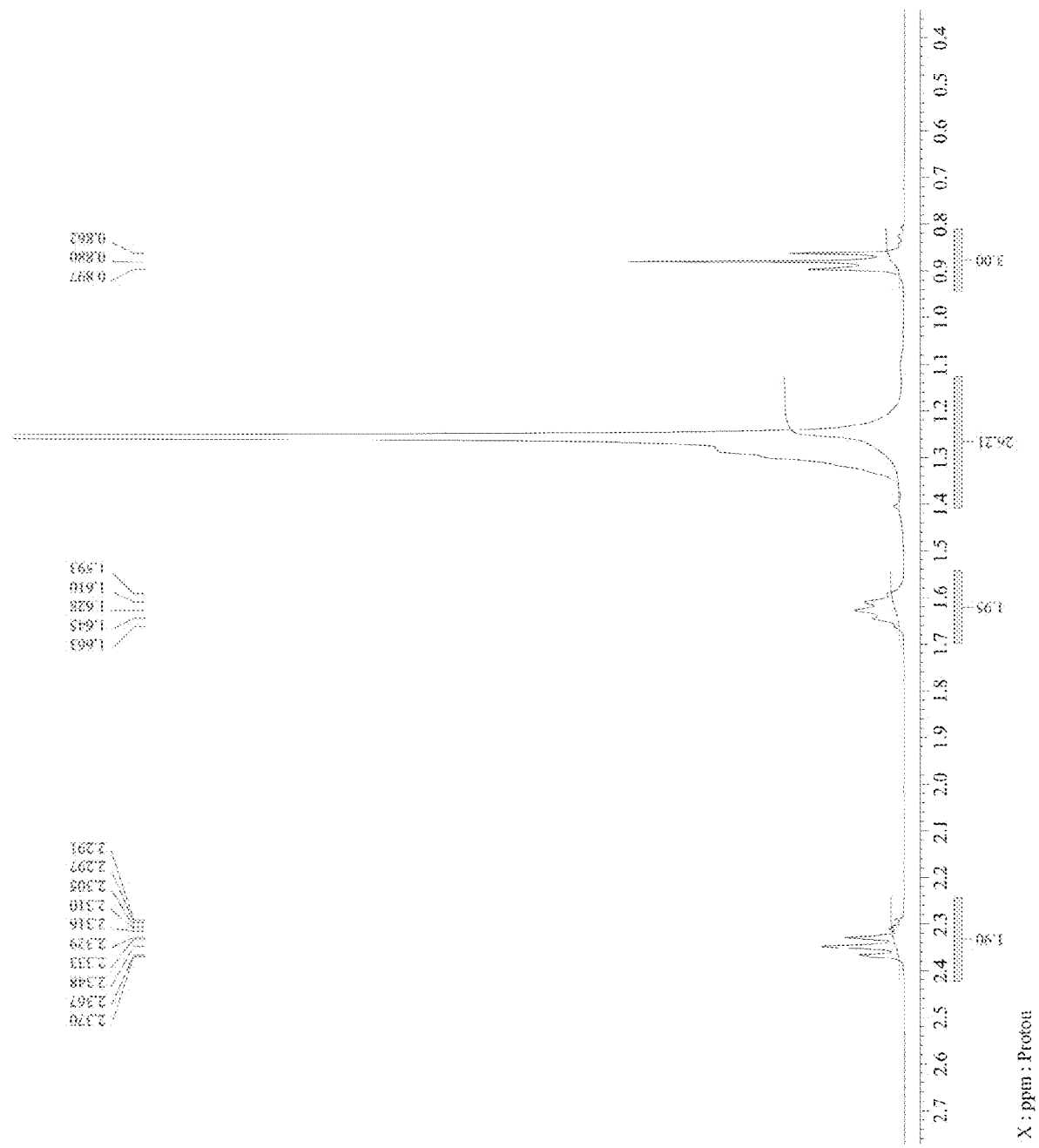

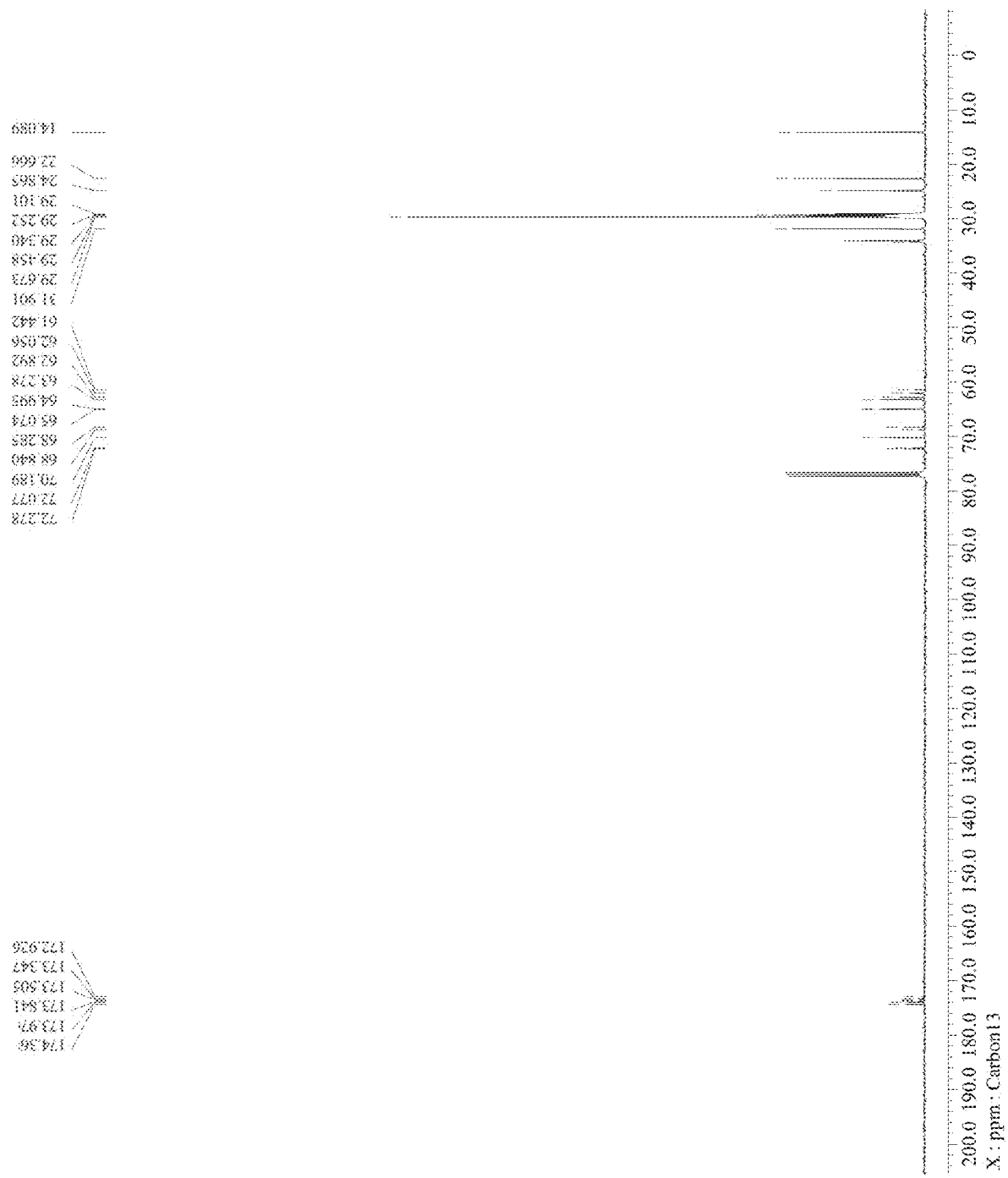

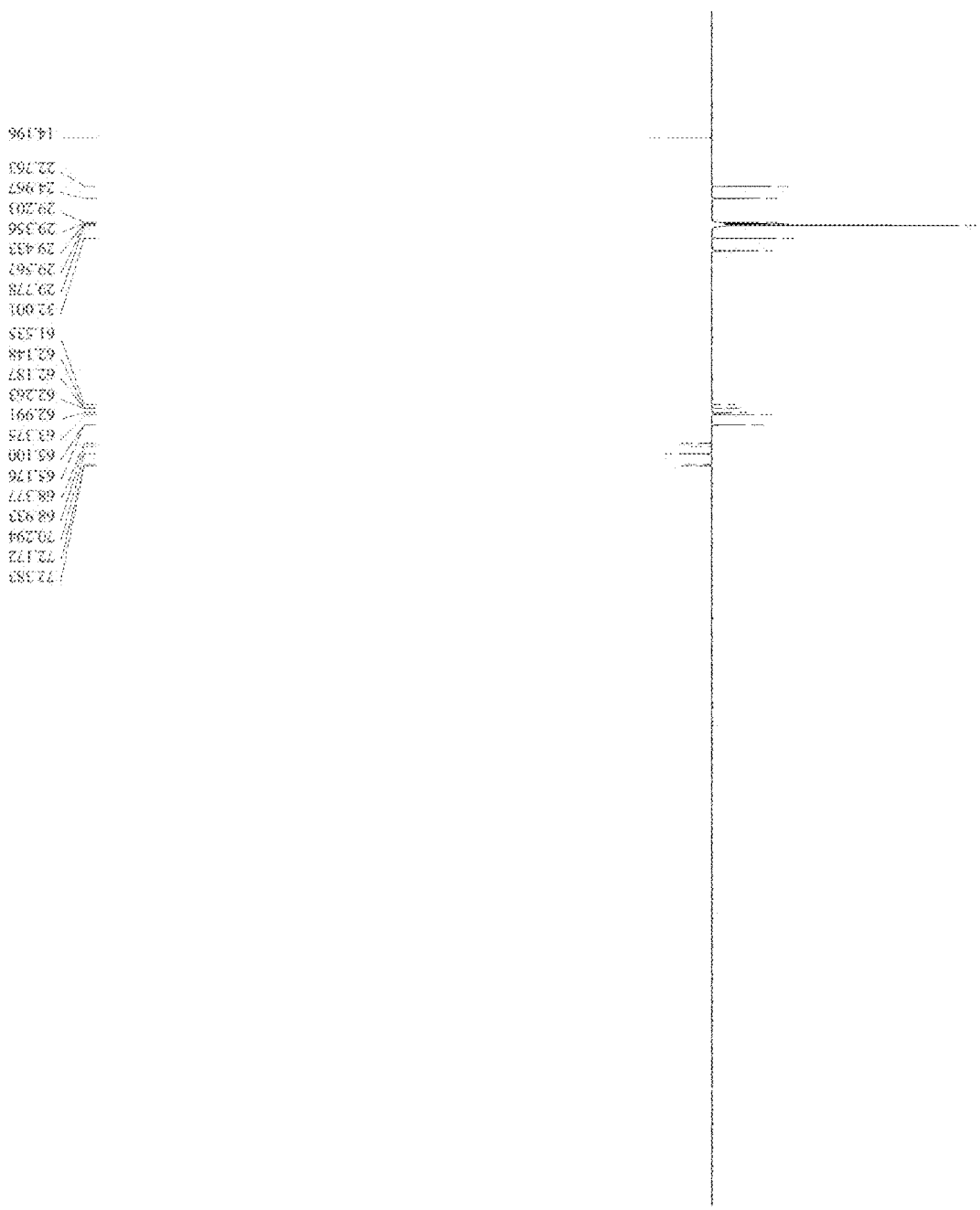

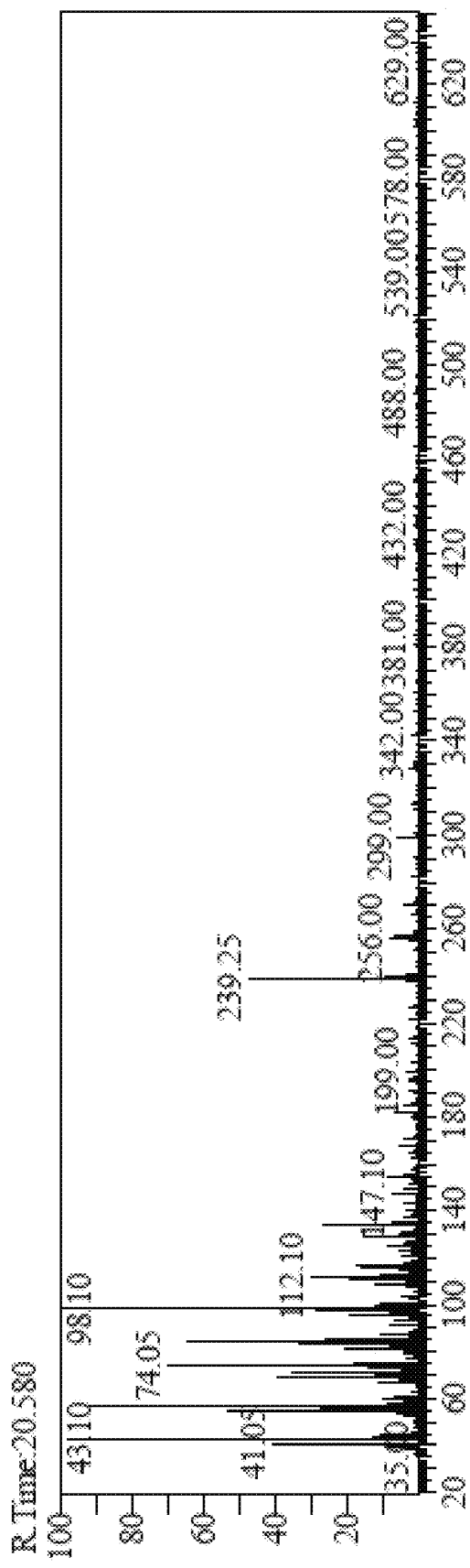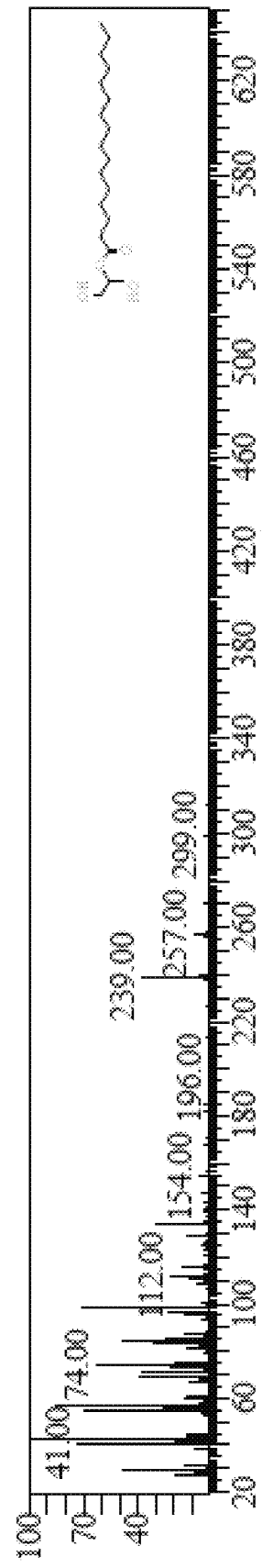
FIG. 6A
FIG. 6B

Instrument ID : GCMS-02
Column ID: SH-Rxi-5 MS 30m X 0.25mm X 0.25μm
Temp Program:50-5-20-300-17.5;
Inj Temp:250°C,Det Temp:300°C;
Flow rate:1.0ml/min,Split ratio:1:50,
Carrier Gas:He,
Diluent:DCM(10.05mg/mL)
Inj.Vol(μL):1.0

| Peak# | Ret.Time | Area | Theoretical Plates | Resolution | Area% |
|---|---|---|---|---|---|
| 1 | 9.056 | 5730 | 145035.652 | 0.000 | 5.019 |
| 2 | 13.457 | 115 | 1377194.358 | 62.428 | 0.101 |
| 3 | 13.708 | 2631 | 49447.090 | 1.719 | 2.305 |
| 4 | 13.825 | 2272 | 2177.557 | 0.164 | 1.990 |
| 5 | 14.022 | 1274 | 285611.740 | 0.305 | 1.116 |
| 6 | 14.127 | 298 | 1106883.017 | 5.065 | 0.261 |
| 7 | 14.909 | 256 | 748816.287 | 7.795 | 0.224 |
| 8 | 17.221 | 7912 | 1266259.098 | 35.539 | 6.930 |
| 9 | 17.356 | 576 | 144915.832 | 1.102 | 0.505 |
| 10 | 17.401 | 955 | 591327.301 | 0.334 | 0.836 |
| 11 | 17.544 | 292 | 1594928.077 | 1.951 | 0.256 |
| 12 | 18.001 | 264 | 785964.298 | 6.678 | 0.231 |
| 13 | 18.329 | 344 | 791701.134 | 4.019 | 0.301 |
| 14 | 18.382 | 1378 | 966688.200 | 0.667 | 1.207 |
| 15 | 18.456 | 1032 | 705621.665 | 0.910 | 0.904 |
| 16 | 18.542 | 495 | 913142.961 | 1.046 | 0.434 |
| 17 | 18.893 | 507 | 1469146.169 | 5.016 | 0.444 |
| 18 | 19.184 | 1170 | 1551032.075 | 4.696 | 1.025 |
| 19 | 19.491 | 438 | 1218909.804 | 4.636 | 0.384 |

| Peak# | Ret.Time | Area | Theoretical Plates | Resolution | Area% |
|---|---|---|---|---|---|
| 20 | 20.118 | 430 | 1416366.347 | 9.070 | 0.376 |
| 21 | 20.295 | 2689 | 1285550.579 | 2.551 | 2.356 |
| 22 | 20.387 | 3125 | 734788.957 | 1.099 | 2.737 |
| 23 | 20.480 | 5106 | 26653.342 | 0.312 | 4.473 |
| 24 | 20.596 | 48616 | 1478620.104 | 0.406 | 42.585 |
| 25 | 21.190 | 320 | 1495941.959 | 8.672 | 0.281 |
| 26 | 21.826 | 5064 | 1143295.672 | 8.428 | 4.436 |
| 27 | 21.929 | 7676 | 947109.026 | 1.202 | 6.724 |
| 28 | 22.159 | 5715 | 25541.757 | 0.712 | 5.006 |
| 29 | 22.260 | 7147 | 1193130.322 | 0.319 | 6.260 |
| 30 | 22.972 | 335 | 1248597.435 | 8.693 | 0.294 |
| Total | | 114162 | | | 100.000 |

*FIG. 6D continued*

Figure 1: Effect of SAVMAX treatment on Vero CCL-81 cells infected with SARS CoV-2. Vero CCL-81 cells were infected with SARS CoV-2 and treated with different dilutions of SAVMAX (fold dilutions) for 72 hours. Virus control (VC) was not treated with the drug. RNA isolated from the respective cells after 72 hours were subjected to qRT-PCR for the RdRp-2 gene target. All data are expressed as mean ± SD (standard deviation) for *n*=3.

*FIG. 8*

WATER SOLUBLE ANTIVIRAL AND ANTIMICROBIAL COMPOUND AND PROCESS FOR PREPARATION THEREOF

CROSS-REFERENCE TO RELATED APPLICATIONS

This application is a U.S. National Phase application, under 35 U.S.C. § 371, of International Application no. PCT/IB2021/053948, with an international filing date of May 10, 2021, and claims benefit of India Application No. 202031050892 filed on Nov. 23, 2020 and India Application No. 202131008965 filed on Mar. 3, 2021; each of which is hereby incorporated by reference for all purposes.

FIELD OF INVENTION

The present invention relates to compounds having antiviral and antimicrobial activity.

BACKGROUND OF INVENTION

A virus is a microorganism and an infectious agent that replicates only inside the living cells of a host cell. When infected, a host cell is forced to rapidly produce thousands of identical copies of the original virus. While outside a host cell, viruses exist in the form of independent particles, or virions, consisting of: (i) the genetic material, i.e., long molecules of DNA or RNA that encode the structure of the proteins by which the virus acts; (ii) a protein coat, the capsid, which surrounds and protects the genetic material; and in some cases (iii) an outside envelope of lipids.

There are very few antiviral medicines which can be used in the treatment of viral infection and normally combination therapy is used.

Also, recently corona virus infection has become a pandemic and highly contagious for human being, the virus spreads through droplets from mouth and nose of the infected people. Once a person is infected by corona virus, the virus remains in the nostrils, in the mouth cavity, in the throat for some time. At this stage, the person is infected and depending upon immunity of the person and load of the virus, infection spreads inside the body and respiratory system. Finally, it creates acute respiratory problem, and the patient goes in the critical stage.

As of now, there is no medicine or any other method to reduce or mitigate the corona virus load in a patient. The treatment regime is based on symptomatic support with various other drugs including retroviral drugs or a combination therapy using hydroxychloroquine and other antiviral agents such as ritonavir and antibacterial agents such as azithromycin.

In view of no established protocol for treatment of corona virus affected patients, the present practice worldwide is to maintain social distancing to avoid getting affected through corona virus laden nasal or oral droplets from an infected person.

Hence, there is an urgent and dire need of developing effective and cost-effective prophylactics which can be highly effective in preventing corona virus spread by way of droplet contact through nasal and oral cavity.

Further, this is also necessary to develop a broad-spectrum antiviral which is effective against many enveloped viruses.

SUMMARY OF INVENTION

An aspect of the present invention relates to compound of Formula A.

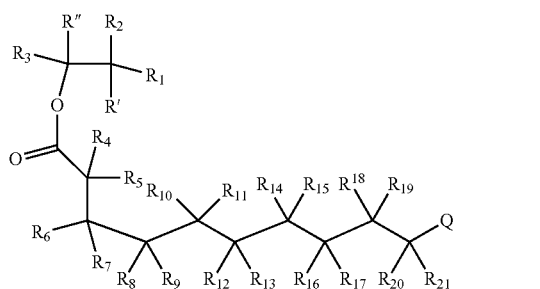

Formula A

Wherein, R' and R" each independently is selected from —H, —OH, alkyl, hydrocarbyl alkyl, alkenyl, alkynyl, phenyl, haloalkanes, fluoroalkane, chloroalkane, bromoalkane, iodoalkane, carbonylaldehyde, haloformylcarbonateester, carboxylatecarboxyl, carboalkoxy, hydroperoxy, peroxy, ether, hemiacetal, hemiketal, acetal, ketal, orthoester, methylenedioxyorthocarbonate ester, carboxylic anhydride, carboxamide, primary amine, tertiary amine, 40 ammonium ion, primary ketimine, secondaryketimine, imineimide, azidazo, cyanate, nitrate, nitrilenitrite, nitro, oxime, pyridyl, carbamate, thiol, sulfide, disulfide, sulfinyl, sulfonyl, sulfino, sulfo, thiocyanate, isothiocyanate, carbonothioyl, thioster, provided that R' is —OH, when R" is —H, alkyl, hydrocarbylalkyl, alkenyl, alkynyl, phenyl, haloalkanes, fluoroalkane, chloroalkane, bromoalkane, iodoalkane, carbonylaldehyde, haloformylcarbonateester, carboxylatecarboxyl, carboalkoxy, hydroperoxy, peroxy, ether, hemiacetal, hemiketal, acetal, ketal, orthoester, methylenedioxyorthocarbonate ester, carboxylic anhydride, carboxamide, primary amine, tertiary amine, 40 ammonium ion, primary ketimine, secondaryketimine, imineimide, azidazo, cyanate, nitrate, nitrilenitrite, nitro, oxime, pyridyl, carbamate, thiol, sulfide, disulfide, sulfinyl, sulfonyl, sulfino, sulfo, thiocyanate, isothiocyanate, carbonothioyl, thioster;

or

R" is —OH, when R' is —H, alkyl, hydrocarbylalkyl, alkenyl, alkynyl, phenyl, haloalkanes, fluoroalkane, chloroalkane, bromoalkane, iodoalkane, carbonylaldehyde, haloformylcarbonateester, carboxylatecarboxyl, carboalkoxy, hydroperoxy, peroxy, ether, hemiacetal, hemiketal, acetal, ketal, orthoester, methylenedioxyorthocarbonate ester, carboxylic anhydride, carboxamide, primary amine, tertiary amine, 40 ammonium ion, primary ketimine, secondaryketimine, imineimide, azidazo, cyanate, nitrate, nitrilenitrite, nitro, oxime, pyridyl, carbamate, thiol, sulfide, disulfide, sulfinyl, sulfonyl, sulfino, sulfo, thiocyanate, isothiocyanate, carbonothioyl, thioster;

$R_1$-$R_{21}$ each independently is selected from —H or alkyl;

Q is selected from —$CH_3$,

-continued

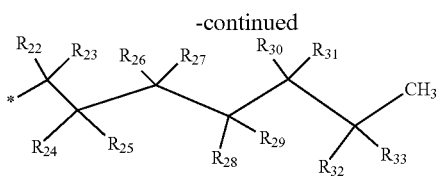

wherein * represents point of attachment and $R_{22}$-$R_{33}$ each independently is selected from —H or alkyl.

Another aspect of the present invention relates to compounds of Formula I.

Formula I

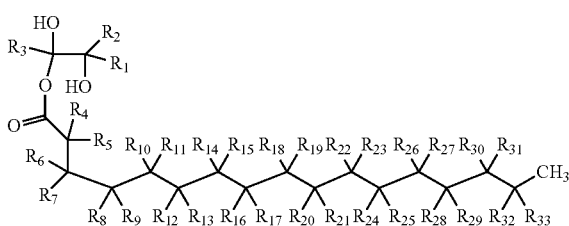

wherein $R_1$-$R_{33}$ each independently is selected from —H or alkyl.

In an aspect the invention relates to compound of Formula II (1,2-dihydroxy ethyl heptadecanoate).

Formula II

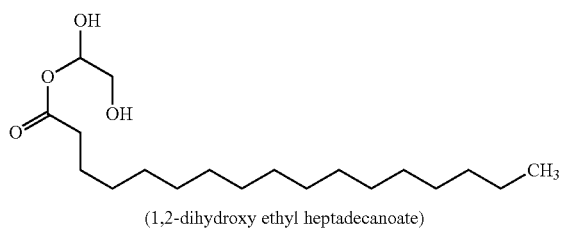

(1,2-dihydroxy ethyl heptadecanoate)

The invention also encompasses a method to prepare the aforesaid compounds.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

FIG. 3 (FIGS. 3A, 3B and 3C) illustrates $D_2O$ Exchange NMR Spectrum results of compound of Formula II.

DETAILED DESCRIPTION OF INVENTION

Figure 1:
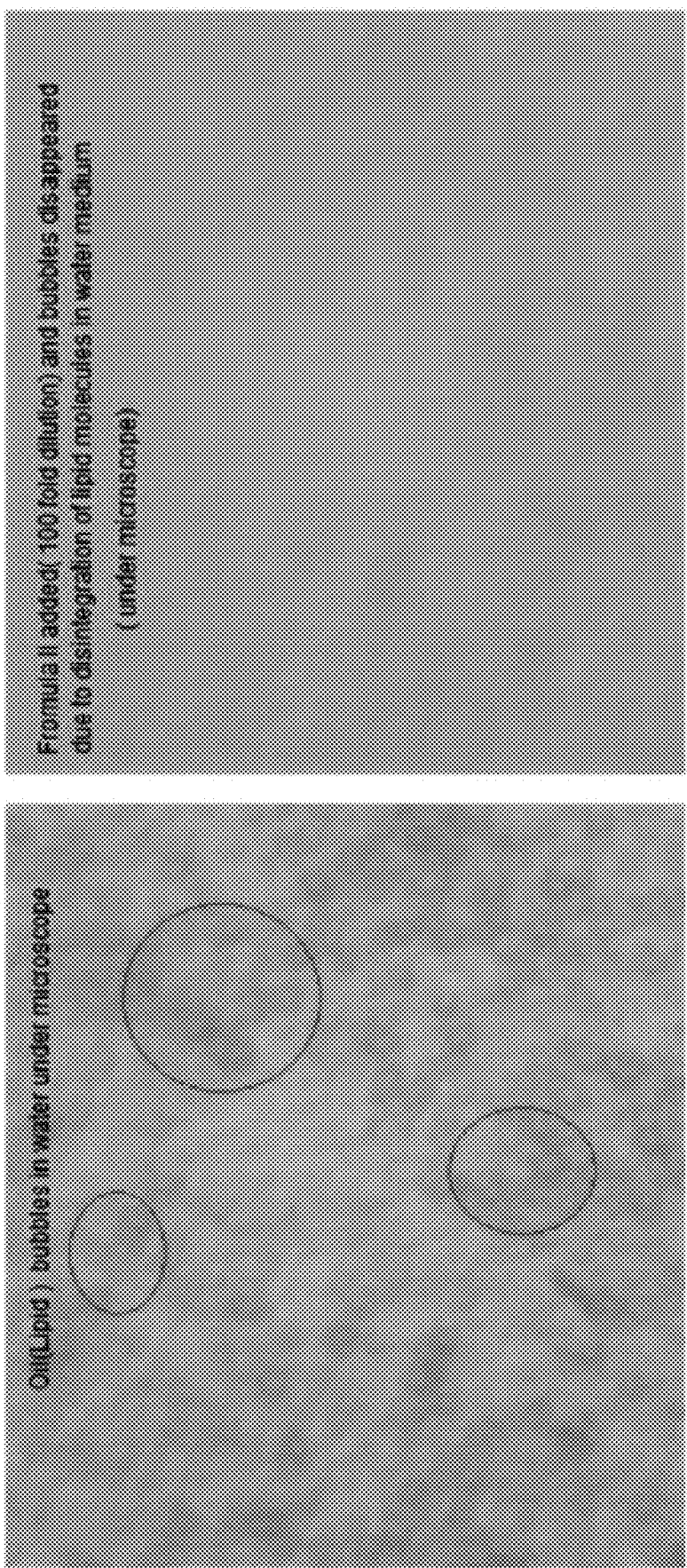
FIG. 1 illustrates disruption of lipids (oil) bubbles in water by compound of Formula II.

The present invention relates to compound of Formula A having antiviral and antimicrobial activity. Particularly, the compounds are effective against various viruses including all enveloped viruses such as SARS CoV-2, influenza virus such as parainfluenza 3, avian influenza virus, microbes such as *Escherichia coli, Staphylococcus aureus, Bacillus subtilis, Candida albicans.*

The structure of compound of Formula A is:

Formula A

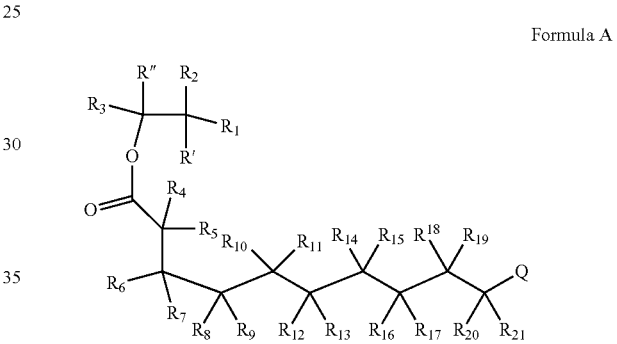

wherein R' and R" each independently is selected from —H, —OH or alkyl, hydrocarbyl alkyl, alkenyl, alkynyl, phenyl, haloalkanes, fluoroalkane, chloroalkane, bromoalkane, iodoalkane, carbonylaldehyde, haloformylcarbonateester, carboxylatecarboxyl, carboalkoxy, hydroperoxy, peroxy, ether, hemiacetal, hemiketal, acetal, ketal, orthoester, methylenedioxy-orhtocarbonate ester, carboxylic anhydride, carboxamide, primary amine, tertiary amine, 40 ammonium ion, primary ketimine, secondaryketimine, imineimide, azidazo, cyanate, nitrate, nitrilenitrite, nitro, oxime, pyridyl, carbamate, thiol, sulfide, disulfide, sulfinyl, sulfonyl, sulfino, sulfo, thiocyanate, isothiocyanate, carbonothioyl, thioster, provided that, R' is —OH, when R" is —H, alkyl, hydrocarbylalkyl, alkenyl, alkynyl, phenyl, haloalkanes, fluoroalkane, chloroalkane, bromoalkane, iodoalkane, carbonyl aldehyde, haloformylcarbonateester, carboxylatecarboxyl, carboalkoxy, hydroperoxy, peroxy, ether, hemiacetal, hemiketal, acetal, ketal, orthoester, methylenedioxy-orthocarbonate ester, carboxylic anhydride, carboxamide, primary amine, tertiary amine, 40 ammonium ion, primary ketimine, secondaryketimine, imineimide, azidazo, cyanate, nitrate, nitrilenitrite, nitro, oxime, pyridyl, carbamate, thiol, sulfide, disulfide, sulfinyl, sulfonyl, sulfino, sulfo, thiocyanate, isothiocyanate, carbonothioyl, thioster;

or

R" is —OH, when R' is —H, alkyl, hydrocarbylalkyl, alkenyl, alkynyl, phenyl, haloalkanes, fluoroalkane, chloroalkane, bromoalkane, iodoalkane, carbonylaldehyde, haloformylcarbonateester, carboxylatecarboxyl, carboalkoxy, hydroperoxy, peroxy, ether, hemiacetal, hemiketal, acetal, ketal, orthoester, methylenedioxyorthocarbonate ester, carboxylic anhydride, carboxamide, primary amine, tertiary amine, 40 ammonium ion, primary ketimine, secondaryketimine, imineimide, azidazo, cyanate, nitrate, nitrilenitrite, nitro, oxime, pyridyl, carbamate, thiol, sulfide, disulfide, sulfinyl, sulfonyl, sulfino, sulfo, thiocyanate, isothiocyanate, carbonothioyl, thioster;

$R_1$-$R_{21}$ each independently is selected from —H or alkyl;

Q is selected from —$CH_3$,

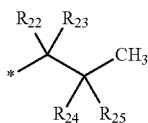

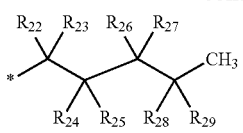

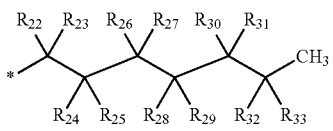

wherein * represents point of attachment and $R_{22}$-$R_{33}$ each independently is selected from —H or alkyl.

The compounds encompassed by the present invention are represented by the structures of Formula I, Formula I-A, Formula I-B, Formula I-C, Formula I-D, Formula I-E, Formula I-F, Formula I-G (Formula I to Formula I-G).

Formula I

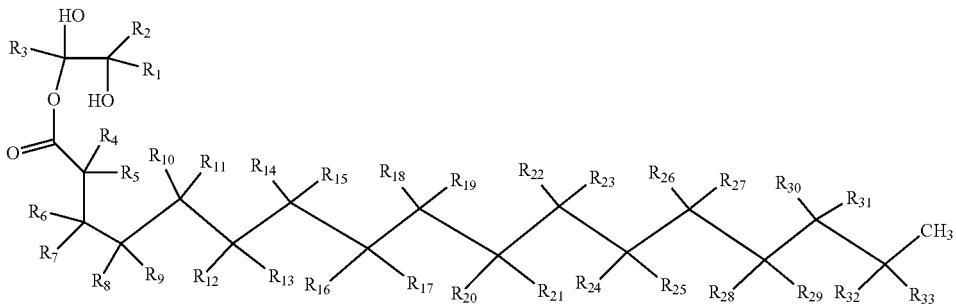

Formula I-A

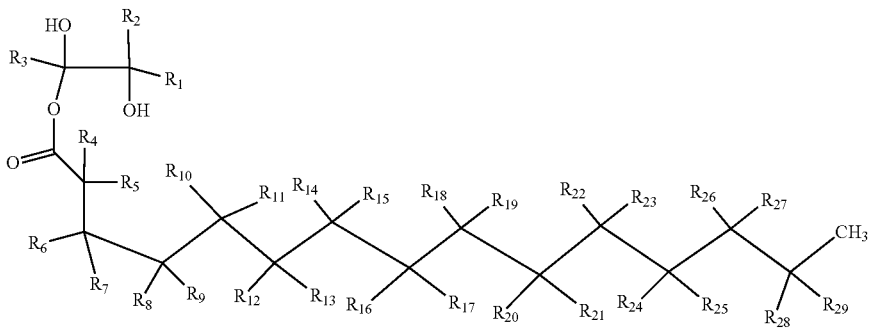

Formula I-B

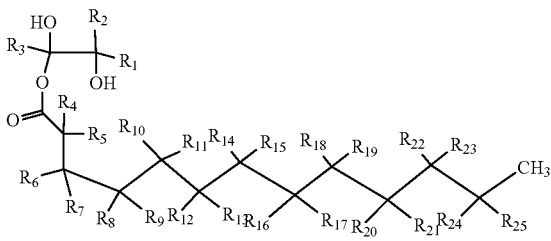

Formula I-C

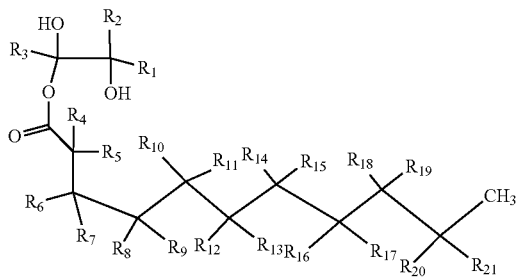

-continued

Formula I-D

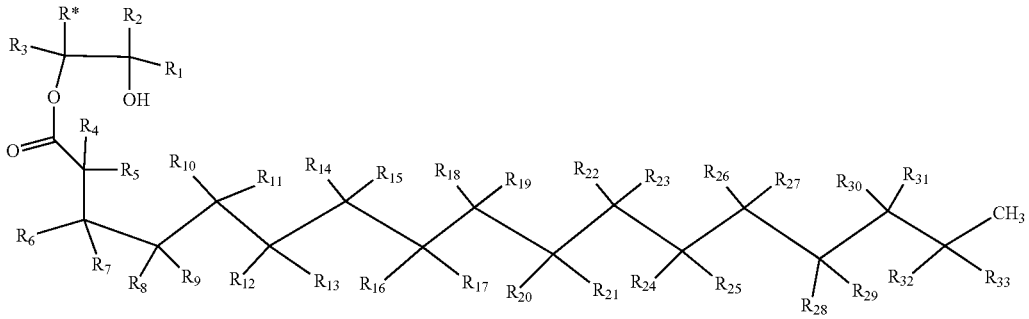

Formula I-E

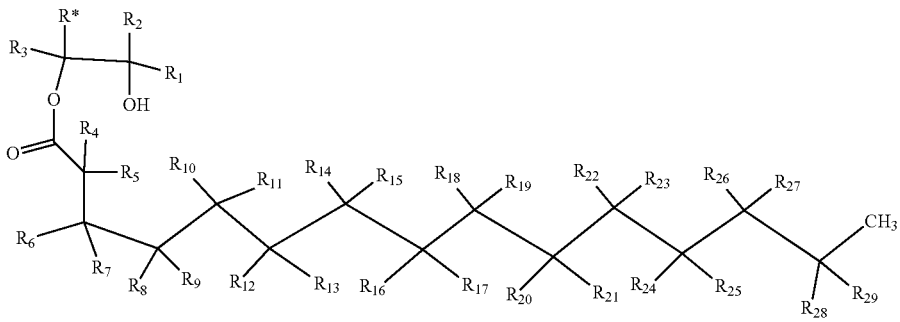

Formula I-F

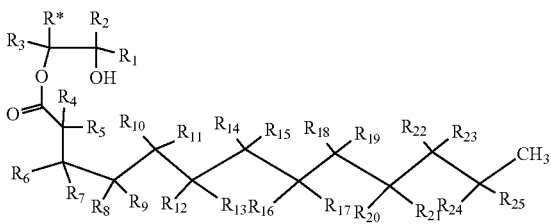

Formula I-G

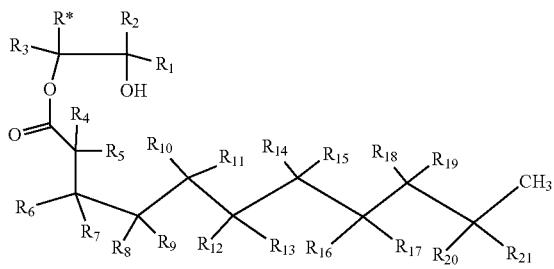

wherein, $R_1$-$R_{33}$ each independently is selected from —H or alkyl; and

R" is —H, alkyl, hydrocarbylalkyl, alkenyl, alkynyl, phenyl, haloalkanes, fluoroalkane, chloroalkane, bromoalkane, iodoalkane, carbonylaldehyde, haloformylcarbonateester, carboxylatecarboxyl, carboalkoxy, hydroperoxy, peroxy, ether, hemiacetal, hemiketal, acetal, ketal, orthoester, methylenedioxyorthocarbonate ester, carboxylic anhydride, carboxamide, primary amine, tertiary amine, 40 ammonium ion, primary ketimine, secondaryketimine, imineimide, azidazo, cyanate, nitrate, nitrilenitrite, nitro, oxime, pyridyl, carbamate, thiol, sulfide, disulfide, sulfinyl, sulfonyl, sulfino, sulfo, thiocyanate, isothiocyanate, carbonothioyl, thioster.

Preferably, the invention relates to compound of Formula I.

Formula I

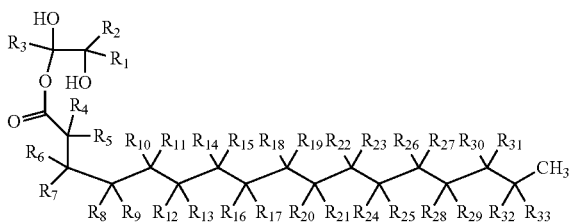

wherein, $R_1$-$R_{33}$ each independently is selected from but not limited to —H, alkyl.

In an embodiment of the present invention, compound of Formula A comprises a single —OH group.

In a preferred embodiment, the structure of the compound having antiviral and antimicrobial activity is represented by Formula II (1,2-dihydroxyethyl heptadecanoate).

Formula II

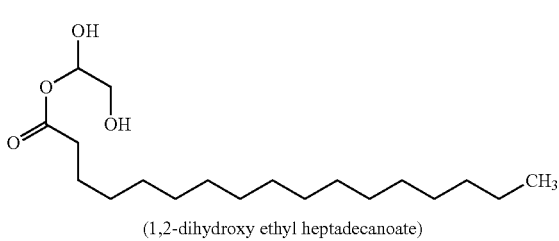

(1,2-dihydroxy ethyl heptadecanoate)

The chemical formula of compound of Formula II is $C_{19}H_{38}O_4$ and molecular weight is 330.51.

Compounds of Formula A, Formula I to I-G or Formula II are amphiphilic with hydrophobic head and hydrophilic tail. The macromolecular structure of the compounds is micelle or reverse micelle.

The derivatives of heptadecanoate have antiviral activity. The dihydroxyethyl esters and monohydroxyethyl esters encompassed by the above formulae have antiviral activity. The compounds also have antimicrobial activity.

The compounds have $C_{10}$-$C_{25}$ long aliphatic chains, wherein the long aliphatic chains consist of carbon, hydrogen and oxygen.

The compounds have water soluble or water dispersible medium or long chain aliphatic chain esters.

The compounds of the present invention form micelles in an aqueous solution. The micelle substance, whose ionic heads form an outer shell in contact with water, while nonpolar tails are sequestered in, within a super molecule assembly.

The compounds are water soluble edible emulsified wherein either of the starting material, such as fatty acid ester including glycerol stearate/glycerol oleate/glycerol laurate are completely insoluble in water.

The compounds form micelle and have HLB value≥10. The micelle is an aggregate (or supramolecular assembly) of new substance dispersed in a liquid, forming a colloidal suspension. This water soluble/dispersible micelle has the nonpolar and polar phases and can have reversed roles wherein the orientation of emulsifier/surfactant molecules are inverted so that the head groups point into the enclosed volume containing the polar phase. This can include a micelle with head hydrophilic groups pointing outward in the water solution phase or water colloidal phase.

The compounds have virucidal and bactericidal action on contact thereof. The compounds are characterized by a lipophilic tail end and a hydrophilic head end. The antiviral mode of action of the compound is like a soap, which kills virus and microbes in minutes on contact.

The compounds encompassed by the invention are non-toxic. Particularly, compound of Formula II is non-toxic oral, LD 50@ 4000 mg per kg wt of rat and mice. The compounds are non-toxic intraperitoneal, LD 50 @ 400 mg per kg wt of rat and mice.

An embodiment of the invention discloses a method of preparation of the compounds. Ester is mixed in an alcohol with application of heat to obtain an ester-alcohol solution. Water is added to the ester-alcohol solution with vigorous stirring to obtain compound of Formula A or compound of Formula I to I-G or compound of Formula II depending on the reactants used. Residual precursor reagents (ester, alcohol) is present or absent along with compound of Formula A or compound of Formula I to I-G or Formula II.

Ester and alcohol are preferably present in a ratio of 1:0.001 to 200:1. Heating of the solution is carried out up to 60 minutes, preferably 15-60 minutes.

The following equation is followed by the materials used in the process.

$$X:Y:Z \text{ to } X\hat{}a:Y\hat{}B:Z\hat{}c \text{ to } (X-a):(Y-b):(Z-c),$$

$$\text{or } (X-a):(Y-b):(Z-c)\hat{}n, \text{ or } (X-a)^{n-1}:(Y-b)n^{n-1}:(Z-c)_{n-1},$$

$$\text{or } (X-a)^{n+1}:(Y-b)^{n+1}:(Z-c)^{n+1} \text{ or } (X+a)^n:(Y+b)^n:(Z+c)_n, \text{etc}$$

Whereas X=alcohol in g/ml; Y=ester in g, Z=water in g/ml and X, Y, Z are >0, and ranges from a, b, c n are integer numbers whereas a, b, c is greater than 0, n is >0.

The compounds are obtained as a semi liquid or semi solid pasty substance. The density of the substance largely depends on the quantity of water added either during synthesis or after synthesis.

Any alcohol can be used in the synthetic procedure. Preferably, most common alcohols such as methanol, ethanol, propanol and butanol or combination thereof is used for the synthesis.

Fatty acid esters are selected from one or more of glycerol monostearate, glycerol monolaurate, glycerol monooleate, Glycerin Fatty Acid Esters, Acetic Acid Esters of Monoglycerides, Lactic Acid Esters of Monoglycerides, Citric Acid Esters of Monoglycerides, Succinic Acid Esters of Monoglycerides, Diacetyl Tartaric Acid Esters of Monoglycerides, Polyglycerol Esters of Fatty Acids, Polyglycerol Polyricinoleate, Sorbitan Esters of Fatty Acids, Propylene Glycol Esters of Fatty Acids, Sucrose Esters of Fatty Acids, Calcium Stearoyl Di Lactate, Lecithin, Enzyme Digested Lecithin/Enzyme Treated Lecithin, 2-Arachidonoylglycerol, Ascorbyl palmitate, Ascorbyl stearate, Cetylmyristoleate, Cetyl palmitate, Di-deuterated linoleic acid ethyl ester, Diglyceride, Ethyl decadienoate, Ethyl decanoate, Ethyl eicosapentaenoic acid, Ethyl macadamiate, Ethylhexyl palmitate, Fatty acid methyl ester, Glyceryl hydroxystearate, Glycol distearate, Isopropyl jojobate, Methyl ricinoleate, Mono- and diglycerides of fatty acids, Monoctanoin, Monoglyceride, Monolaurin, 2-Oleoylglycerol, Omega-3 acid ethyl esters, Polyglycerol, polyricinoleate, Sorbitan monooleate, Sorbitanmonopalmitate, Virodhamine.

Other esters that can be used are selected from one or more of allyl hexanoate, benzyl acetate, bornyl acetate, Butyl acetate, Butyl butyrate, Butyl propanoate, Ethyl acetate, Ethyl benzoate, Ethyl butyrate, Ethyl hexanoate, Ethyl cinnamate, Ethyl Ethanoate, Ethyl formate, Ethyl heptanoate, Ethyl isovalerate, Ethyl lactate, Ethyl nonanoate, Ethyl pentanoate, Geranyl acetate, Geranyl butyrate, Geranyl pentanoate, Isobutyl acetate, Isobutyl formate, Isoamyl acetate, Isopropyl acetate, Linalyl acetate, Linalyl butyrate, Linalyl formate, Methyl acetate, Methyl anthranilate, Methyl benzoate, Methyl butyrate (methyl butanoate), Methyl cinnamate, Methyl pentanoate (methyl valerate), Methyl phenylacetate, Methyl salicylate (oil of wintergreen), Nonyl caprylate, Octyl acetate, Octyl butyrate, Amyl acetate (pentyl acetate), pentyl butyrate (amyl butyrate), pentyl hexanoate (amyl caproate), pentyl pentanoate (amyl valerate), propyl acetate, propyl hexanoate, propyl isobutyrate, terpenyl butyrate.

Preferably, glycerol monostearate, glycerol monooleate or glycerol monolaurate are used.

Preferably, distilled water such as double distilled water is used.

Preferably, the invention covers a process of preparing compound of Formula II (1,2 dihydroxyethyl heptadecanoate). Glycerol monostearate is added to ethanol and the mixture is heated to melt and dissolve glycerol monostearate in ethanol to obtain glycerol monostearate-ethanol solution, which is followed by adding water to obtain compound of Formula II. The temperature of heating is adjusted based on the ambient room temperature and the volume or weight of each ingredients added.

In an embodiment, compound of Formula II is prepared as follows.

Glycerol monostearate is added to ethanol (20:5 w/v) and heated for 15 minutes at a temperature of 40° C. to 200° C. to melt and dissolve glycerol monostearate in ethanol followed by addition of double distilled water in the heated solution while vigorously stirring the same. The final ratio of glycerol monostearate:ethanol:water is 20:5:75 (w/v/v). The resulting substance is white in colour and pasty in appearance. Drying of the pasty substance yields yellowish white amorphous substance of the present invention.

Particularly, the following steps were followed to prepare compound of Formula II.

50 ml of ethanol (99.9% purity) is taken in a 1000 ml glass beaker. 200 g of glycerol monostearate is added to ethanol in the beaker and heated up to 200° C. on a hot plate. The glycerol monostearate is melted and dissolved in ethanol. Then 750 ml of distilled water (room temperature water) is added slowly in the beaker with vigorous stirring with a long spatula. The resultant product is white creamy semi solid substance. The synthesized semi solid creamy substance is water soluble and/or water dispersible which forms a stable colloidal solution in water. The synthesized semi solid substance is foaming material when rinsed in water. This substance has excellent emulsifying property.

In another embodiment, glycerol monooleate based substance is prepared in a similar manner and using the same ratio of 20:5:75 (w/v/v) of glycerol monooleate:ethanol:water.

In another embodiment, glycerol monolaurate based substance is prepared in a similar manner and using the same ratio of 20:5:75 (w/v/v) of glycerol monolaurate:ethanol:water.

The above ratio is not restrictive, and a reasonable ratio range variation of the individual ingredients is within the scope of the invention.

During the reaction process of alcohol and fatty acid esters under heat with follow up addition of excess of water will produce a water soluble/water dispersible colloidal mixture with lipid disrupting properties. The synthesized substance is effective to kill/inactivate the enveloped viruses by disrupting/cleaving the virus (envelop lipid layer and protein).

The hydrolysis reaction takes effect as a sudden change in physical condition of ester after dissolving in alcohol under heat conditions. The alcohol dissolved ester under heating allows the water molecules to initiate hydrolysis of the ester molecules by breaking bonds and synthesis of new compound of Formula A, Formula I to I-G or Formula II with hydrophilic property. This hydrolysis of esters is carried out in the absence of a catalyst.

Another embodiment of the present invention discloses a composition comprising one or more compounds of Formula A, Formula I to I-G or Formula II with one or more pharmaceutically acceptable excipient and optionally one or more active agents selected from antiviral and antimicrobial compounds.

The excipients are selected from binders, fillers, flavoring agents, sweeteners, etc.

An embodiment of the invention relates to stable colloidal solution comprising compound of Formula A, Formula I to I-G or Formula II (1,2-dihydroxy ethyl heptadecanoate) and water.

The invention discloses a method of treatment of infection caused by virus or microbes by administering one or more compounds of Formula A, Formula I to I-G or Formula II, wherein the virus is selected from any virus or enveloped virus or SARS COV 2 virus or parainfluenza virus, paramyxoviruses, Hendra virus (HeV) and Nipah virus (NiV), avian influenza virus, Newcastle disease/Ranikhet disease virus.

A method of inhibition of a virus is also encompassed within the scope of the invention. The method comprises of directly killing the virus by disrupting the lipid layer of the envelope of the virus by administering one or more compounds or composition or colloidal solution of compound of Formula A, Formula I to I-G or Formula II. The compounds enable disintegration of protein of the viral envelop or RNA of the virus is disintegrated.

The invention also relates to the use of the compounds or composition in the treatment of viruses and/or microbes.

The compounds encompassed by the present invention are used as mucosal immunity enhancer:

The compounds of the present invention, particularly compound of Formula II effectively protects the mucosal barrier from invading pathogens including SARS COV 2. Mucosal IgA or secretory IgA (SIgA) are structurally equipped to resist chemical degradation in the harsh environment of mucosal surfaces and the enzymes of host or microbial origin. The compounds give a protective layer on the mucosal layer inside the nasal and mouth cavity from most infectious pathogens entering the host via mucosal surfaces.

The compounds, particularly compound of Formula II indirectly support production of IgA in responses against commensal and pathogenic microbes including SARS COV 2 and other pathogenic viruses which enters through nostrils and mouth cavity.

The compounds encompassed by the present invention, particularly compound of Formula II are used as vaccine adjuvant.

Compound of Formula II can be a very effective vaccine adjuvant for mucosal or epicutaneous delivery of vaccines which help target the inductive sites for IgA responses. The efficacy of such vaccines can be enhanced by compounds of the present invention such as Formula II as vaccine adjuvants capable of supporting the development of SIgA alongside systemic immunity and delivery systems that improve vaccine delivery to the targeted anatomic sites and immune cells.

The compounds encompassed by the present invention, particularly compound of Formula II can also be very useful for curing diseases of animals caused by viruses.

Newcastle Disease (ND)/Ranikhet Disease (RD)

This is an acute viral disease of poultry characterized by involvement of respiratory system, drop in egg production and mortality as high as 100% in severe cases. This virus has zoonotic effect and can causes human deaths.

Paramyxoviruses are also responsible for a range of diseases in other animal species, for example canine distemper virus (dogs), phocine distemper virus (seals), cetacean morbillivirus (dolphins and porpoises), Newcastle disease virus (birds), and rinderpest virus (cattle). Some paramyxoviruses such as the henipa viruses are zoonotic pathogens, occurring naturally in an animal host, but also is able to infect humans.

Hendra virus (HeV) and Nipah virus (NiV) in the genus Henipavirus have emerged in humans and livestock in Australia and Southeast Asia. Both viruses are contagious, highly virulent, and capable of infecting a number of mammalian species and causing potentially fatal disease. Due to the lack of a licensed vaccine or antiviral therapies, HeV and NiV are designated as Biosafety level (BSL) 4 agents. The genomic structure of both viruses is that of a typical paramyxovirus.

The compounds can be effective in the eradication of such and other viruses.

It has been found that compound of Formula II is able to reduce 92% of mortality rate in birds infected with avian influenza. Compound of Formula II was tested on poultry birds infected with avian influenza. The mortality rate is 550 per day in 14000 flocks. Compound of Formula II at a ratio of 1:9 with water. 30 ml was administered per 100 birds per day and the mortality rate was reduced to 92%. This shows the therapeutic antiviral efficacy of compound of Formula II in controlling avian influenza.

The present invention also encompasses a method of treatment of SARS COV 2 by administering compound of Formula A, Formula I to Formula I-G or Formula II to a patient in need thereof.

The present invention also encompasses a method of treatment of parainfluenza virus by administering compound of Formula A, Formula I to Formula I-G or Formula II to a patient in need thereof.

The present invention also encompasses a method of treatment of microbial infection by administering compound of Formula A, Formula I to Formula I-G or Formula II to a patient in need thereof.

Compound of Formula A or II can be provided in a dose as low as 1200 fold of 20% active ingredient described in Formula 1 and formula 2.

The compounds of the present invention can also be provided along with standard therapies available for antiviral and antimicrobial treatment.

An embodiment of the present invention discloses a method of inhibition of a virus. The method comprises of disrupting the lipid layer of the envelope of the virus by administering compound of Formula A, Formula I to Formula I-G or Formula II to a patient.

The lipid disrupting action of the compound of Formula II was tested and it was found that the compound resulted in lipid degradation indicating antiviral action of the compounds.

Model demonstrations of lipid degradation:
1. Mustard oil/butter/sunflower oil/mineral oils were taken in various concentrations. Few drops of 100 fold diluted compound of Formula II was added. The oily character of the molecules immediately diminished and there was no trace of oil in the petriplates when washed by water post treatment.
2. These above model demonstrations showed the lipid disrupting characteristics of the antiviral compounds.

FIG. 1 illustrates disruption of lipids (oil) bubbles in water by compound of Formula II.

The compounds of the present invention can be used in various ways. Some non-limiting examples are provided below.
1. Nasal drop: The compound of the present invention is administered as a nasal drop to wet the entire nostril passage and allowing to keep the liquid for at-least 20 seconds.
2. Oral administration: The compound is used as a mouth wash and gargle for few minutes to kill the viruses in the mouth and throat.

The compound can be orally administered which will pass through the elementary canal and eventually reach intestine for absorption in the blood, the blood will carry these administered molecules in contact with the virus in the lung cells and eventually kill them by disintegrating the capsid outside the cell before penetration.

3. It is also possible to have parenteral composition for administration.
4. The compounds of the present invention can be used as preventive remedy (prophylactic) from infections. The compound can be used as disinfectant/protective barrier on the hand, toy surfaces or any surface to kill the enveloped viruses which comes in contact with the compound. As long as the cream, lotion, liquid formulation of the antiviral/antimicrobial compound is attached on the surface, the surface remains virus free and will kill all viruses in contact previously present on the surface or invading the surface.

The dihydroxy alcohol esters have antiviral activity, particularly dihydroxyethyl fatty acid esters are antiviral.

Further, dihydroxyethyl and hydroxyethyl compounds of the following esters have antiviral activity.

Glycerin Fatty Acid Esters, Acetic Acid Esters of Monoglycerides, Lactic Acid Esters of Monoglycerides, Citric Acid Esters of Monoglycerides, Succinic Acid Esters of Monoglycerides, Diacetyl Tartaric Acid Esters of Monoglycerides, Polyglycerol Esters of Fatty Acids, Polyglycerol Polyricinoleate, Sorbitan Esters of Fatty Acids, Propylene Glycol Esters of Fatty Acids, Sucrose Esters of Fatty Acids, Calcium Stearoyl Di Lactate, Lecithin, Enzyme Digested Lecithin/Enzyme Treated Lecithin, 2-Arachidonoylglycerol, Ascorbyl palmitate, Ascorbyl stearate, Cetylmyristoleate, Cetyl palmitate, Di-deuterated linoleic acid ethyl ester, Diglyceride, Ethyl decadienoate, Ethyl decanoate, Ethyl eicosapentaenoic acid, Ethyl macadamiate, Ethylhexyl palmitate, Fatty acid methyl ester, Glyceryl hydroxystearate, Glycol distearate, Isopropyl jojobate, Methyl ricinoleate, Mono- and diglycerides of fatty acids, Monoctanoin, Monoglyceride, Monolaurin, 2-Oleoylglycerol, Omega-3 acid ethyl esters, Polyglycerol, polyricinoleate, Sorbitan monooleate, Sorbitan monopalmitate, Virodhamine, allyl hexanoate, benzyl acetate, bornyl acetate, Butyl acetate, Butyl butyrate, Butyl propanoate, Ethyl acetate, Ethyl benzoate, Ethyl butyrate, Ethyl hexanoate, Ethyl cinnamate, Ethyl Ethanoate, Ethyl formate, Ethyl heptanoate, Ethyl isovalerate, Ethyl lactate, Ethyl nonanoate, Ethyl pentanoate, Geranyl acetate, Geranyl butyrate, Geranyl pentanoate, Isobutyl acetate, Isobutyl formate, Isoamyl acetate, Isopropyl acetate, Linalyl acetate, Linalyl butyrate, Linalyl formate, Methyl acetate, Methyl anthranilate, Methyl benzoate, Methyl butyrate (methyl butanoate), Methyl cinnamate, Methyl pentanoate (methyl valerate), Methyl phenylacetate, Methyl salicylate (oil of wintergreen), Nonyl caprylate, Octyl acetate, Octyl butyrate, Amyl acetate (pentyl acetate), Pentyl butyrate (amyl butyrate), Pentyl hexanoate (amyl caproate), Pentyl pentanoate (amyl valerate), Propyl acetate, Propyl hexanoate, Propyl isobutyrate, terpenyl butyrate.

EXAMPLES

The following examples illustrate the invention but are not limiting thereof.

Example 1: Preparation of 1,2-dihydroxy ethyl heptadecanoate (Formula II)

50 ml of ethanol (99.9% purity) was taken in a 1000 ml glass beaker. 200 g of glycerol monostearate was added to ethanol in the beaker and heated up to 200° C. on a hot plate. The glycerol monostearate was melted and dissolved in ethanol. Then 750 ml of distilled water (room temperature water) was added slowly in the beaker with vigorous stirring with a long spatula to result in 1,2-dihydroxy ethyl heptadecanoate. The resultant product was white creamy semi solid substance. The synthesized semi solid creamy substance was water soluble and/or water dispersible and formed a stable colloidal solution in water.

Example 2

50 ml of ethanol (99.9% purity) was taken in a 1000 ml glass beaker. 200 g of glycerol monooleate was added to ethanol in the beaker and heated up to 200° C. on a hot plate.

The glycerol monooleate was melted and dissolved in ethanol. Then 750 ml of distilled water (room temperature water) was added slowly in the beaker with vigorous stirring with a long spatula. The resultant product was white creamy semi solid substance. The synthesized semi solid creamy substance was water soluble and/or water dispersible and formed a stable colloidal solution in water.

Example 3

50 ml of ethanol (99.9% purity) was taken in a 1000 ml glass beaker. 200 g of glycerol monolaurate was added to ethanol in the beaker and heated up to 200° C. on a hot plate. The glycerol monolaurate was melted and dissolved in ethanol. Then 750 ml of distilled water (room temperature water) was added slowly in the beaker with vigorous stirring with a long spatula. The resultant product was white creamy semi solid substance. The synthesized semi solid creamy substance was water soluble and/or water dispersible and formed a stable colloidal solution in water.

Characterization Studies:

Characterization of Compound of Formula II:

A. NMR Spectroscopy.

Figure 2A:
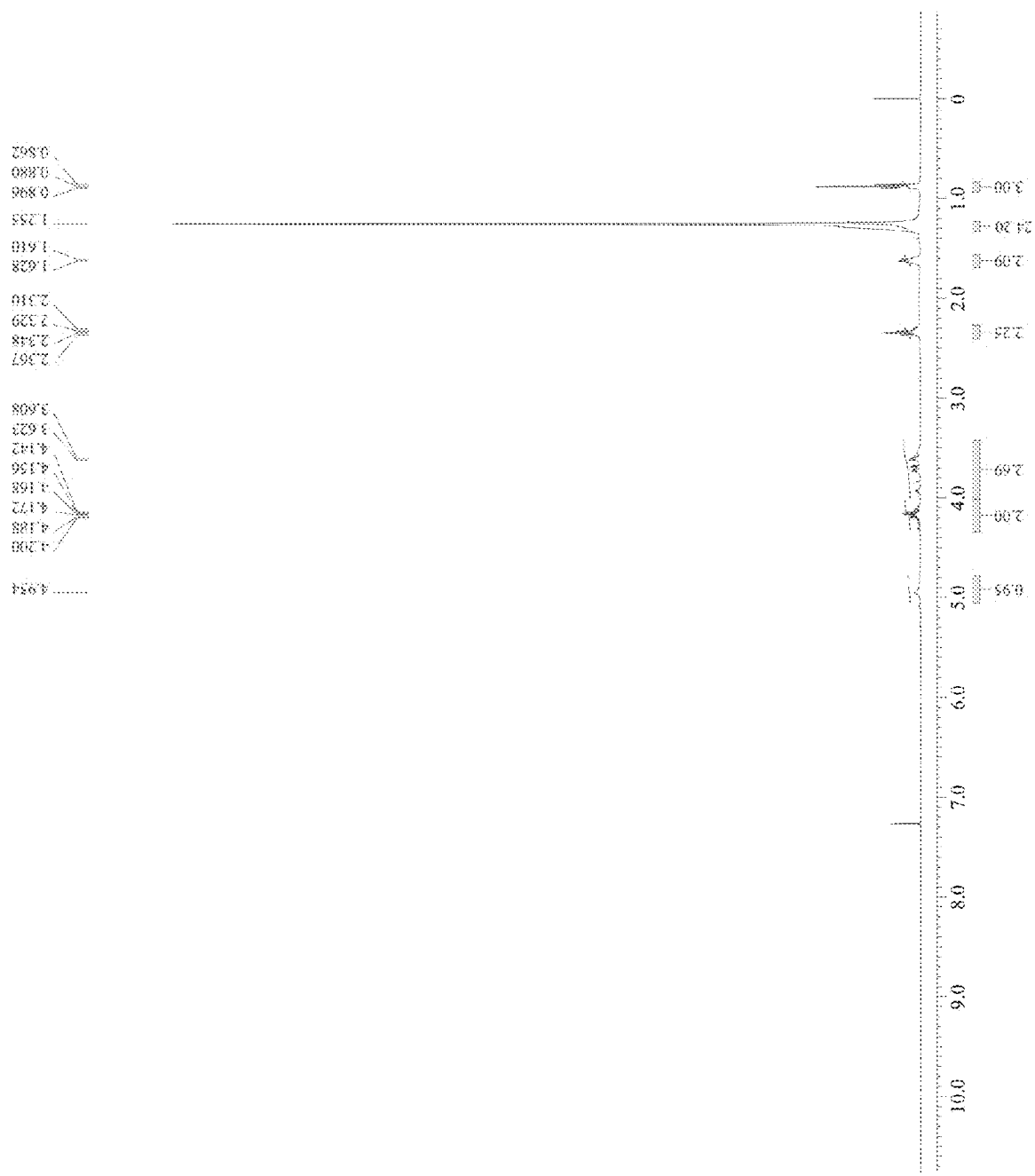
FIG. 2 (FIGS. 2A, 2B and 2C) illustrates $^1$H NMR Spectrum results of compound of Formula II.
Figure 2B:
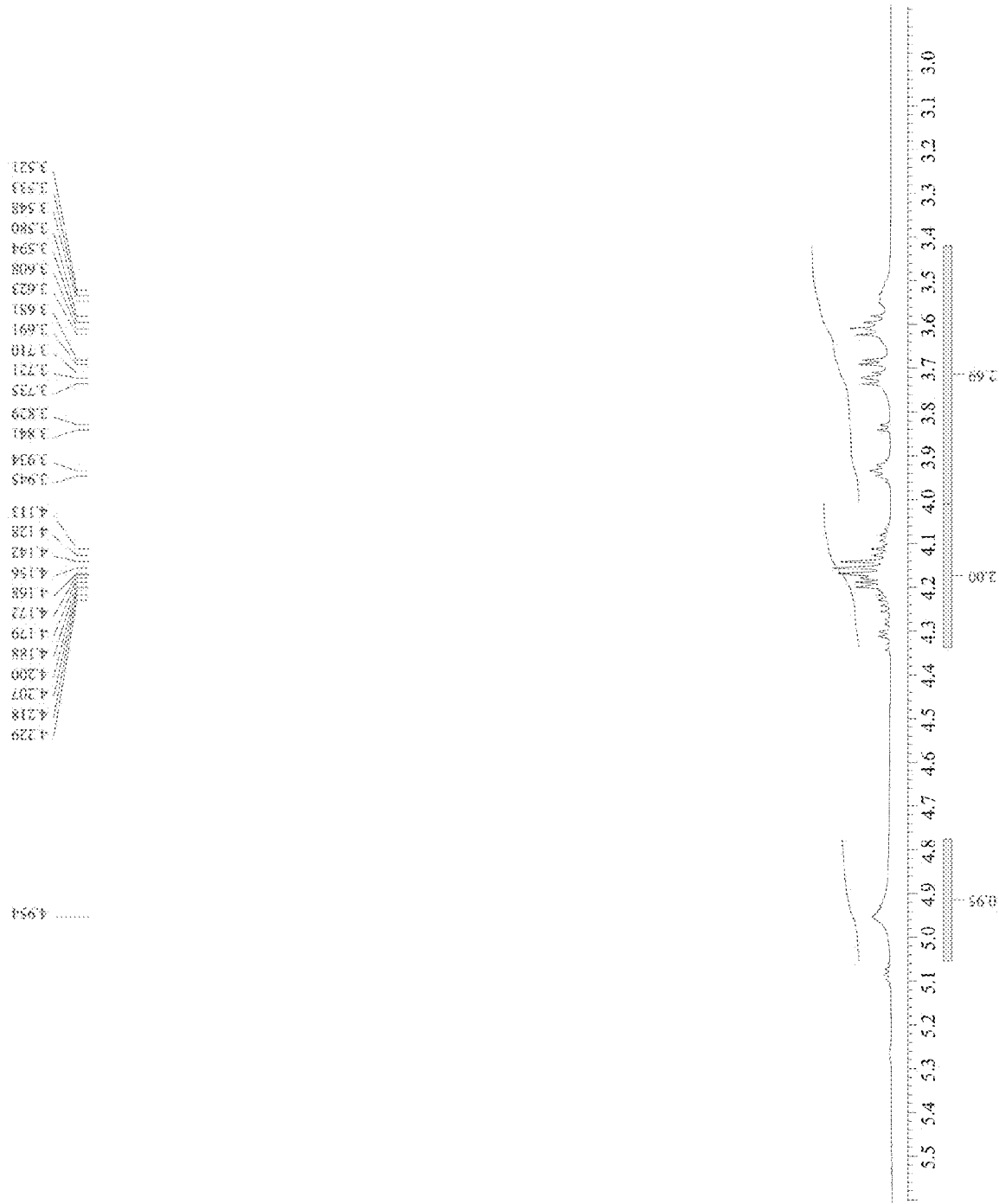

1. $^1$H NMR Spectrum:

Proton ($^1$H) NMR chemical shifts are reported on the δ scale in ppm. Protons were identified from the atom numbers of Formula II. FIG. 2 (FIGS. 2A, 2B and 2C) illustrates $^1$H NMR Spectrum results.

| Processing Parameters: | |
| --- | --- |
| sexp( 0.3[Hz], 0.0[s] ) | Instrument - NMR-400 MHz(JEOL) |
| trapezoid( 0[%], 0[%], 80[%], 100[%] ) | Instrument id - NMR-01 |
| zerofill( 4 ) | Solvent = CHLOROFORM-D |
| fft( 1, TRUE, TRUE ) | Spectrometer = JNM-ECZ400S/L1 |
| machinephase | Experiment = proton.jxp |
| ppm | Acquisition Parameter |
| auto_reference( 5[%], TRUE ) | X_Domain = Proton |
| phase( −0.67227, 0, 88.96201[%] ) | X_Offset = 7[ppm] |
| | X_Sweep = 9.00576369[kHz] |
| | Scans = 16 |
| | Relaxation_Delay = 2[s] |

TABLE 1

| Proton Position | Chemical Shift in δ (ppm) | Type of Proton | Number of Protons ($^1$H) |
| --- | --- | --- | --- |
| 21 | 0.86-0.89 | —CH$_3$ | 3 |
| 8, 9, 10, 11, 12, 13, 14, 15, 16, 17, 18, 19 & 20 | 1.25 | —CH$_2$ | 26 |
| 7 | 1.61-1.62 | —CH$_2$ | 2 |
| 6 | 2.30-2.36 | —CH$_2$ | 2 |
| 1 | 3.52 | —OH | 1 |
| 2 | 3.58-3.73 | —CH$_2$ | 2 |
| 3 | 4.14-4.18 | —CH | 1 |
| 22 | 4.95 | —OH | 1 |

| J-Coupling | | | |
| --- | --- | --- | --- |
| Position | Integral | Pattern | J |
| 4.95[ppm] | 1 | s | |
| 4.20[ppm] | 2 | m | |
| 3.72[ppm] | 3 | m | |
| 2.33[ppm] | 2 | m | |
| 1.62[ppm] | 2 | q | J1 = 6.9[Hz] |
| 1.25[ppm] | 24 | s | |
| 0.88[ppm] | 3 | t | J1 = 6.8[Hz] |

2. D$_2$O Exchange NMR Spectrum

According to the structure one —CH$_3$ proton, sixteen —CH$_2$ proton and one —CH protons are present in the D$_2$O Exchange spectrum. Two —OH protons got exchanged in D$_2$O Spectrum. Thus, spectrum conforms the structure of the compound of Formula II (1,2-dihydroxyethyl heptadecanoate). FIG. 3 (FIGS. 3A, 3B and 3C) illustrates D$_2$O Exchange NMR Spectrum results.

| Processing Parameters: | |
| --- | --- |
| sexp( 0.3[Hz], 0.0[s] ) | Instrument - NMR-400 MHz(JEOL) |
| trapezoid( 0[%], 0[%], 80[%], 100[%] ) | Instrument id - NMR-01 |
| zerofill( 4 ) | Solvent = CHLOROFORM-D |
| fft( 1, TRUE, TRUE ) | Spectrometer = JNM-ECZ400S/L1 |
| machinephase | Experiment = proton.jxp |
| ppm | Acquisition Parameter |
| auto_reference( 5[%], TRUE ) | X_Domain = Proton |
| | X_Offset = 7[ppm] |

| Processing Parameters: | |
| --- | --- |
| X_Sweep = 9.00576369[kHz] | |
| Scans = 16 | |
| Relaxation_Delay = 2[s] | |

| J-Coupling | | | |
| --- | --- | --- | --- |
| Position | Integral | Pattern | J |
| 4.19[ppm] | 2 | m | |
| 3.89[ppm] | 0 | m | |
| 3.65[ppm] | 1 | m | |
| 2.33[ppm] | 2 | m | |
| 1.63[ppm] | 2 | m | |
| 1.25[ppm] | 26 | s | |
| 0.88[ppm] | 3 | m | |

3. $^{13}$C NMR Spectrum

Carbon (13C) NMR chemical shifts are reported on the δ scale in ppm.

| Processing Parameters: | |
|---|---|
| sexp( 3.0[Hz], 0.0[s] ) | Instrument - NMR-400 MHz(JEOL) |
| trapezoid( 0[%], 0[%], 80[%], 100[%] ) | Instrument id - NMR-01 |
| zerofill( 4 ) | Solvent = CHLOROFORM-D |
| fft( 1, TRUE, TRUE ) | Spectrometer = JNM-ECZ400S/L1 |
| machinephase | Experiment = carbon.jxp |
| ppm | Acquisition Parameter |
| auto_reference( 5[%], TRUE ) | X_Domain = Carbon13 |
| phase( 0.45676, −2.28665, 84.1384[%] ) | X_Offset = 100[ppm] |
| | X_Sweep = 31.56565657[kHz] |
| | Scans = 512 |
| | Relaxation_Delay = 2[s] |

TABLE 2

| Carbon Position | Chemical Shift in δ (ppm) | Type of Carbon | Number of Carbons ($^{13}$C) |
|---|---|---|---|
| 21 | 14.0 | —CH$_3$ | 1 |
| 20 | 22.6 | —CH$_2$ | 1 |
| 7 | 24.8 | —CH$_2$ | 1 |
| 8, 9, 10, 11, 12, 13, 14, 15, 16, 17 & 18 | 29.1-29.6 | —CH$_2$ | 11 |
| 19 | 31.9 | —CH$_2$ | 1 |
| 6 | 34.0 | —CH$_2$ | 1 |
| 2 | 64.9-65.0 | —CH$_2$ | 1 |
| 3 | 70.1 | —CH | 1 |
| 5 | 174.3 | —COO | 1 |

Figure 4B:
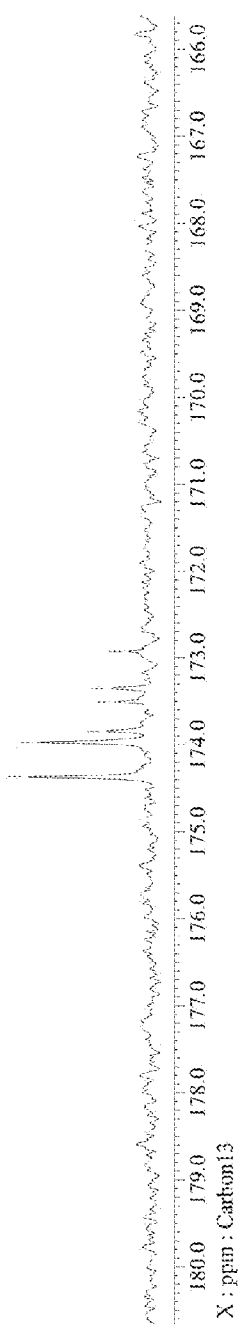
FIG. 4 (FIGS. 4A, 4B, 4C and 4D) illustrates $^{13}$C NMR Spectrum results of compound of Formula II.
Figure 4C:
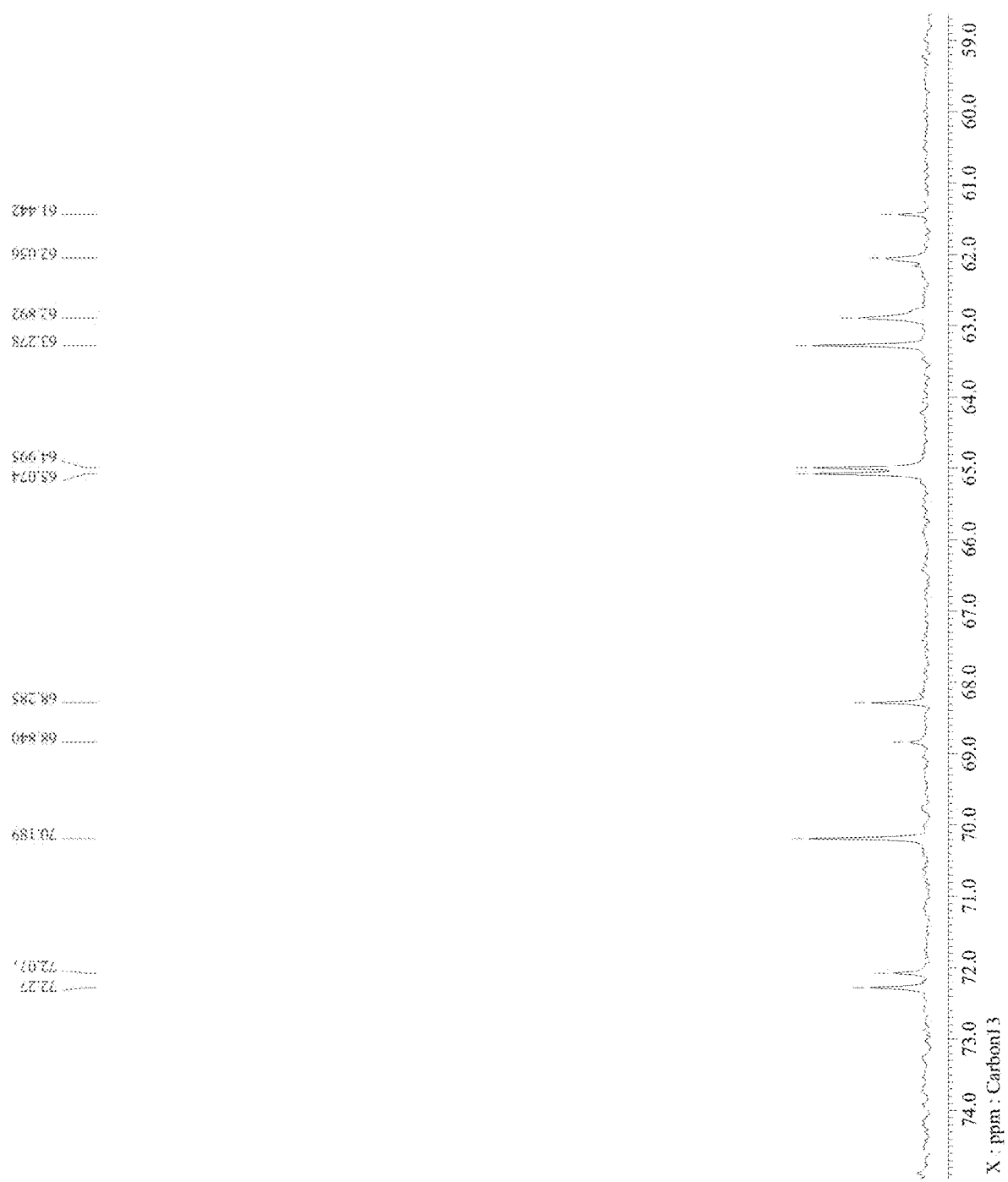
Figure 4D:
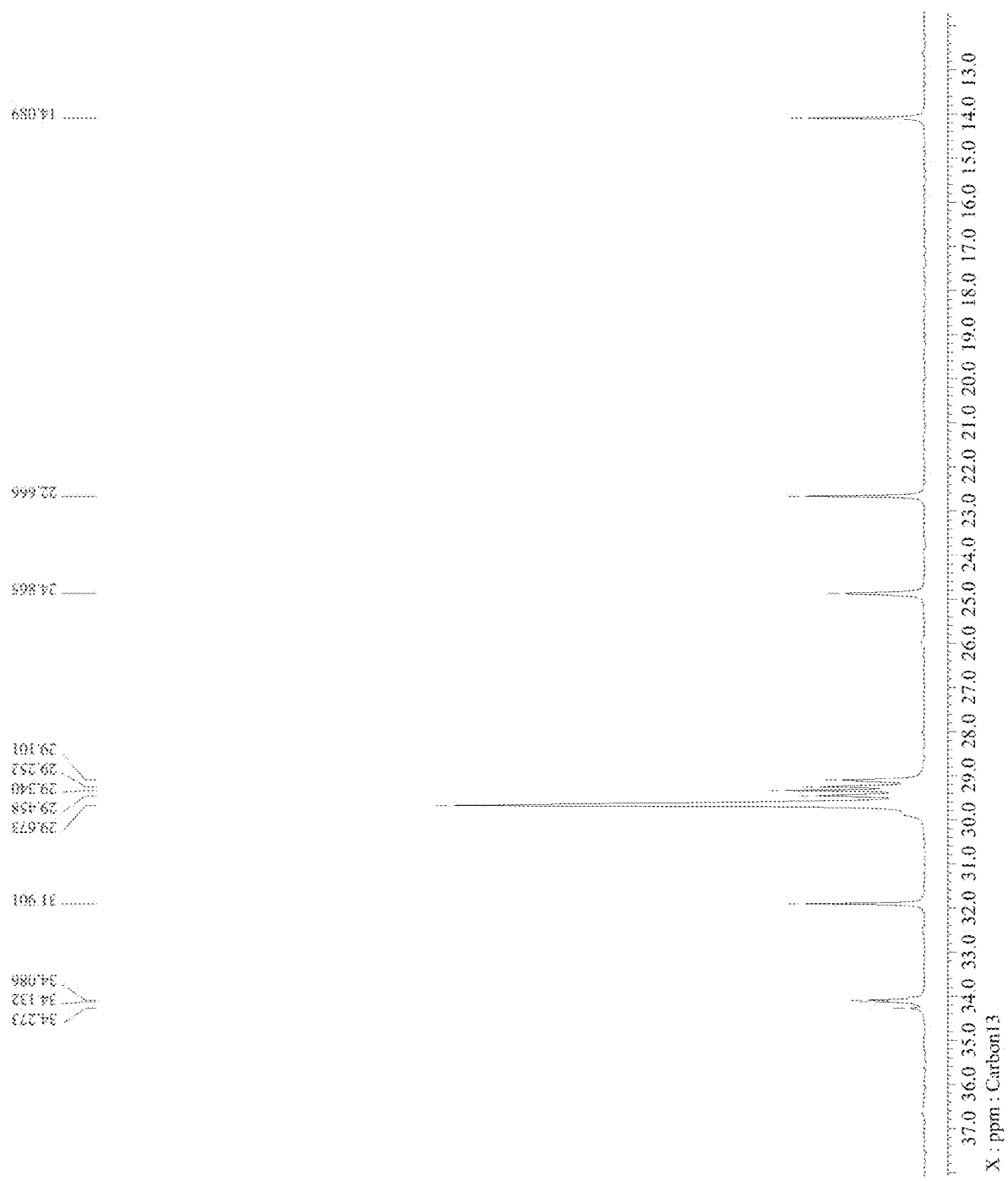

According to the structure one —CH$_3$ carbon, eleven —CH$_2$ carbons, one —CH carbon and one ester (—COO) carbons are present in the spectrum. Thus, spectrum conforms the structure of the compound of Formula II, 1,2-dihydroxyethyl heptadecanoate. FIG. 4 (FIGS. 4A, 4B, 4C and 4D) illustrates $^{13}$C NMR Spectrum results.

4. DEPT NMR Spectrum

Figure 5B:
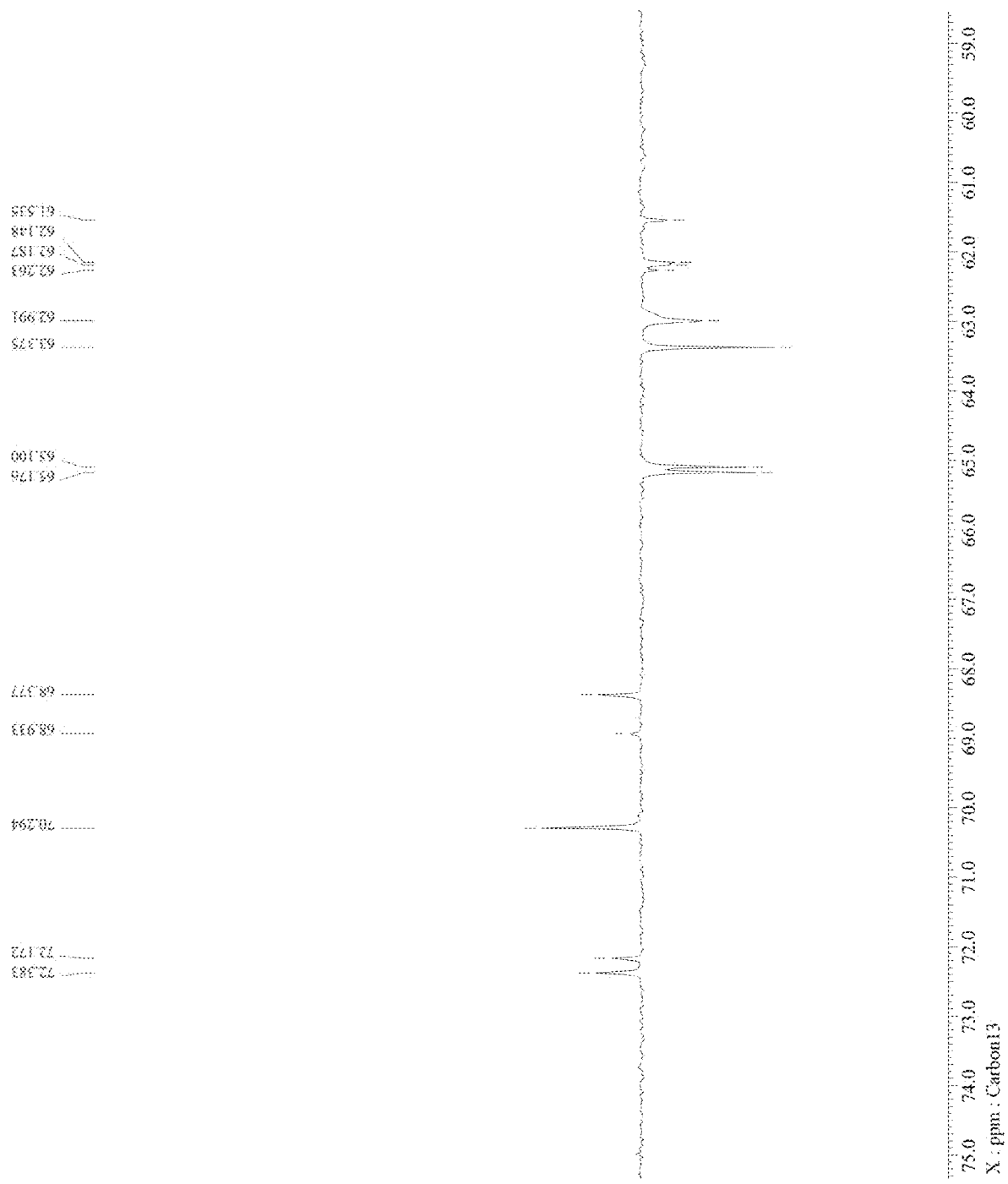
FIG. 5 (FIGS. 5A, 5B and 5C) illustrates the results of DEPT NMR Spectrum, which confirmed the structure of compound of Formula II (1,2-dihydroxyethyl heptadecanoate).
Figure 5C:
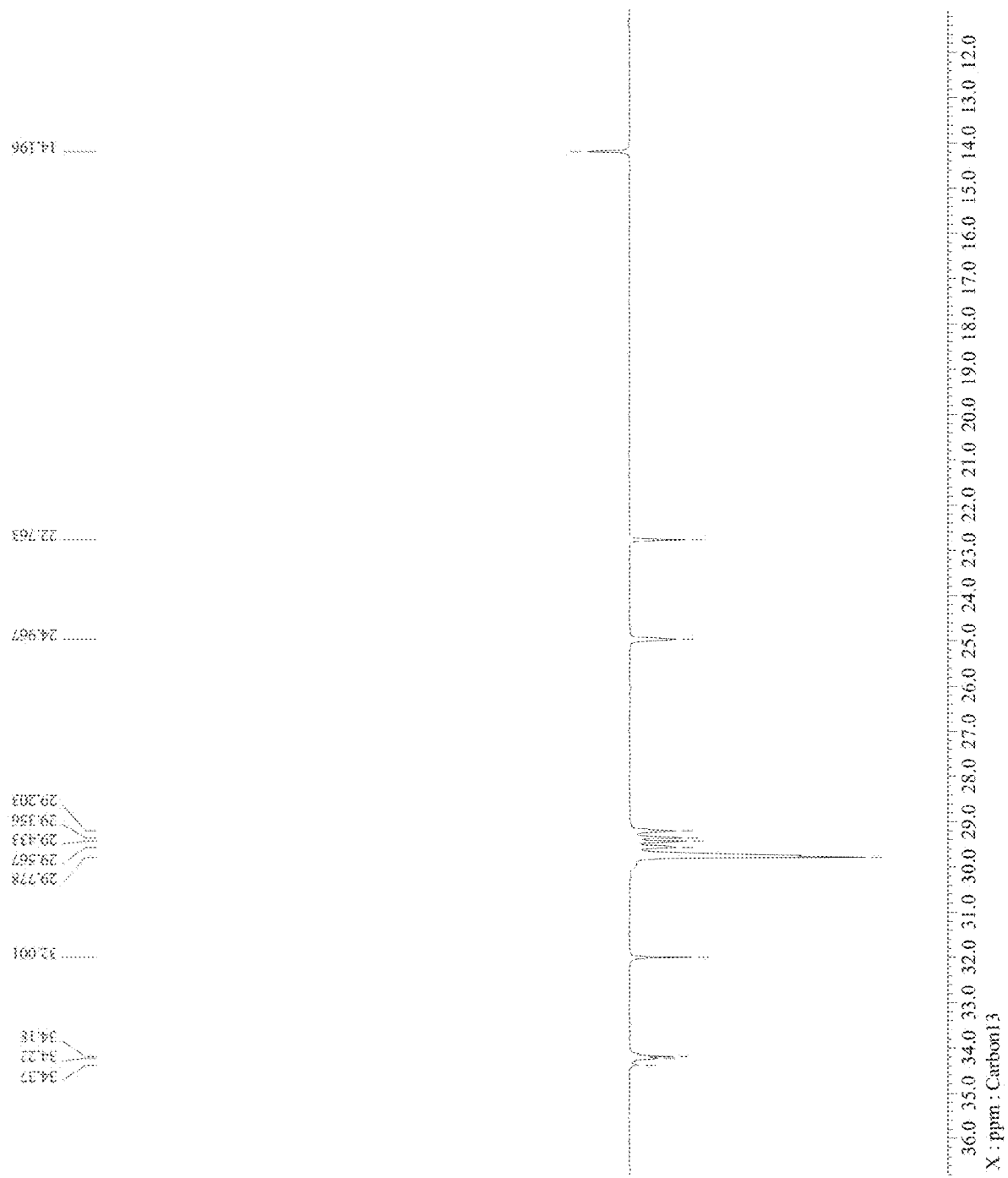

FIG. 5 (FIGS. 5A, 5B and 5C) illustrates the results of DEPT NMR Spectrum, which confirmed the structure of compound of Formula II (1,2-dihydroxyethyl heptadecanoate).

B. GC-Mass spectroscopy:

| Processing Parameters: | |
|---|---|
| sexp(2.0[Hz], 0.0[s]) | Instrument - NMR-400 MHz(JEOL) |
| trapezoid(0[%], 0[%], 80[%], 100[%]) | Instrument id - NMR-01 |
| zerofill(1) | Solvent = CHLOROFORM-D |
| fft(1, TRUE, TRUE) | Spectrometer = JNM-ECZ400S/L1 |
| machinephase | Experiment = dept.jxp |
| ppm | Acquisition Parameter |
| phase(180.77772, 0, 84.19808[%]) | X_Domain = Carbon13 |
| | X_Offset = 100[ppm] |
| | X_Sweep = 31.56565657[kHz] |
| | Scans = 512 |
| | Relaxation_Delay = 2[s] |

The GC-Mass spectroscopy was performed, and the mass observed was 331 m/z in using Electron ionization (EI) technique. The mass observed for the compound, 331 m/z (Molecular ion) are corresponding to $C_{19}H_{38}O_4$.

Figure 6C:
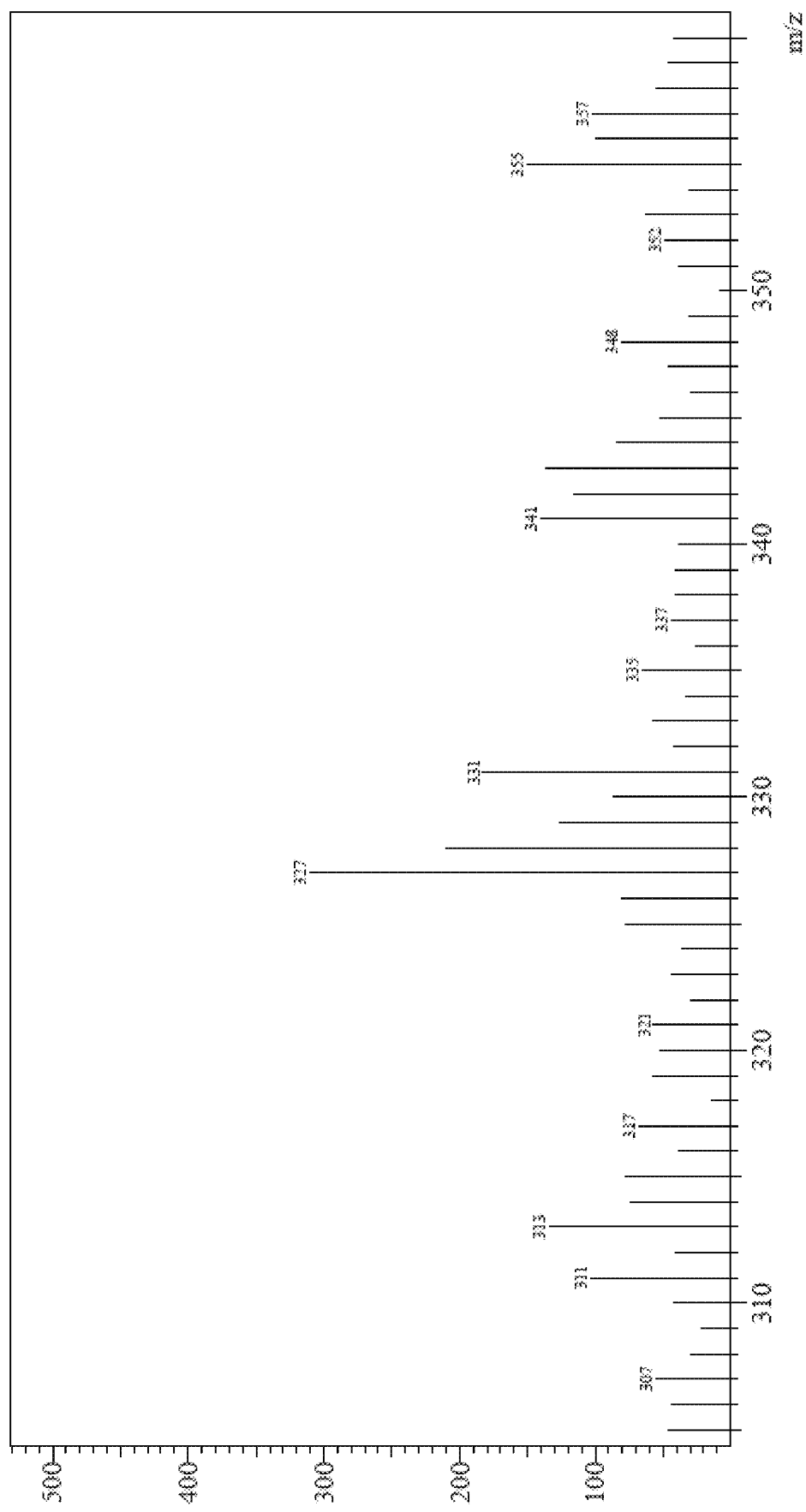
FIG. 6 (FIGS. 6A, 6B, 6C and 6D) illustrates the results of GC-Mass spectroscopy of compound of Formula II.
Figure 6D:
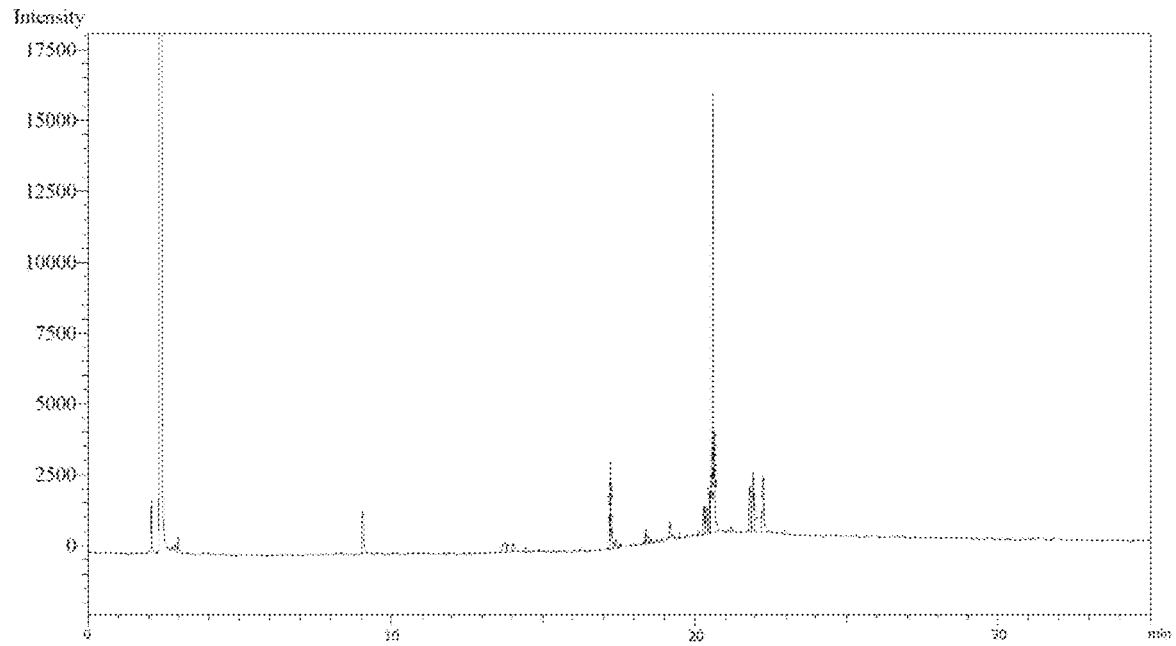

The Mass spectrum confirms the molecular mass of the base structure and molecular formula of the structure. FIG. 6 (FIGS. 6A, 6B, 6C and 6D) illustrates the results of GC-Mass spectroscopy.

C. Infrared Spectrum
1. The bands at 3,385.42 CM$^{-1}$ correspond to the —OH group present in the molecule.
2. Presence of C=O and C—O bands in the range of 1737.55 CM$^{-1}$ and 1047.16 CM$^{-1}$ shows the presence of ester groups in the molecule.
3. The empirical structure has hydroxy and ester groups.

Figure 7:
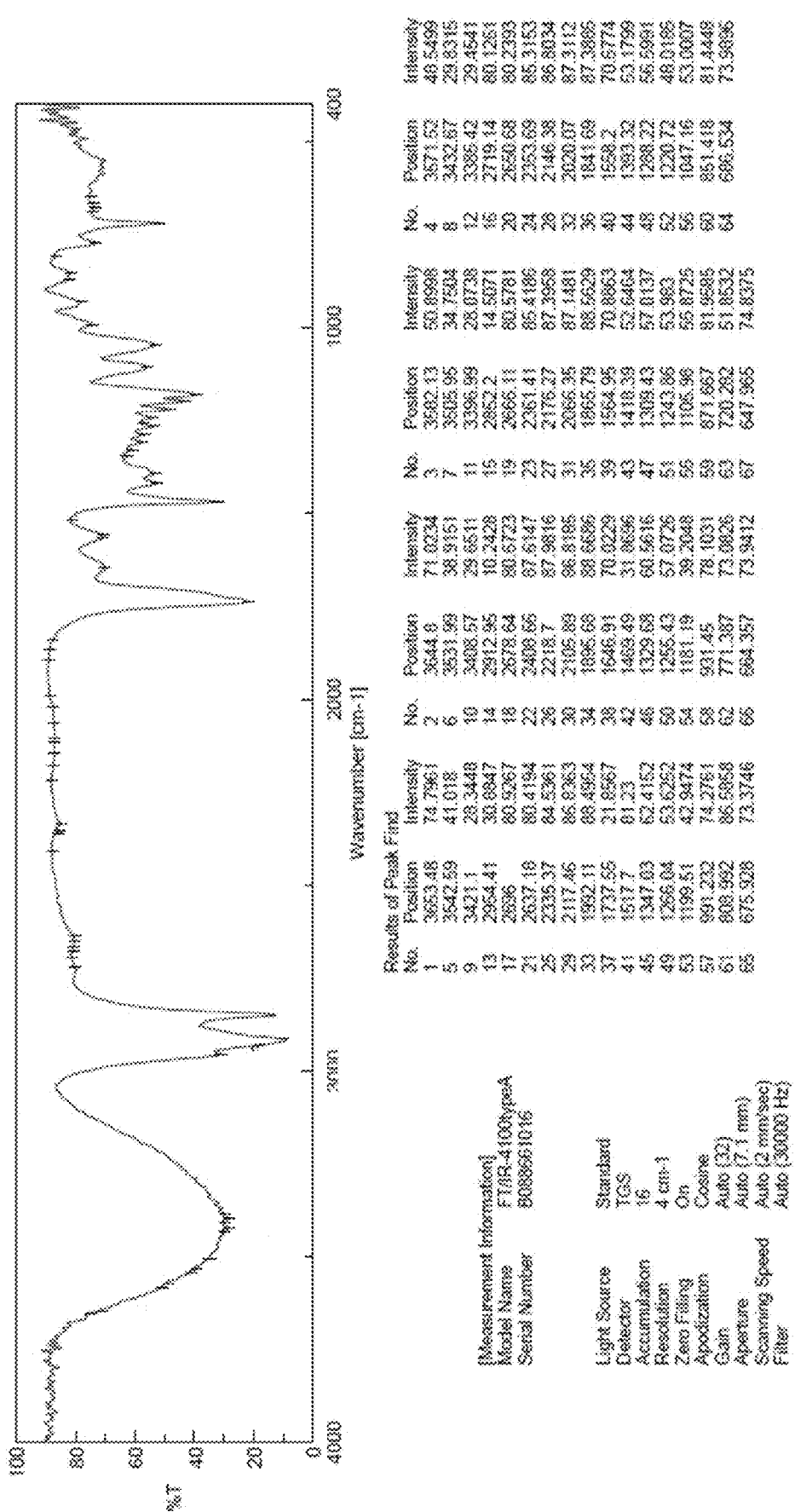
FIG. 7 illustrates Infrared spectroscopy results of compound of Formula II.

The IR spectrum confirmed the presence of hydroxy group and ester groups and hence confirmed the structure of Formula II. FIG. 7 illustrates Infrared spectroscopy results.

Activity of the Compounds

D. Activity Against SARS CoV-2 Virus

Figure 8:
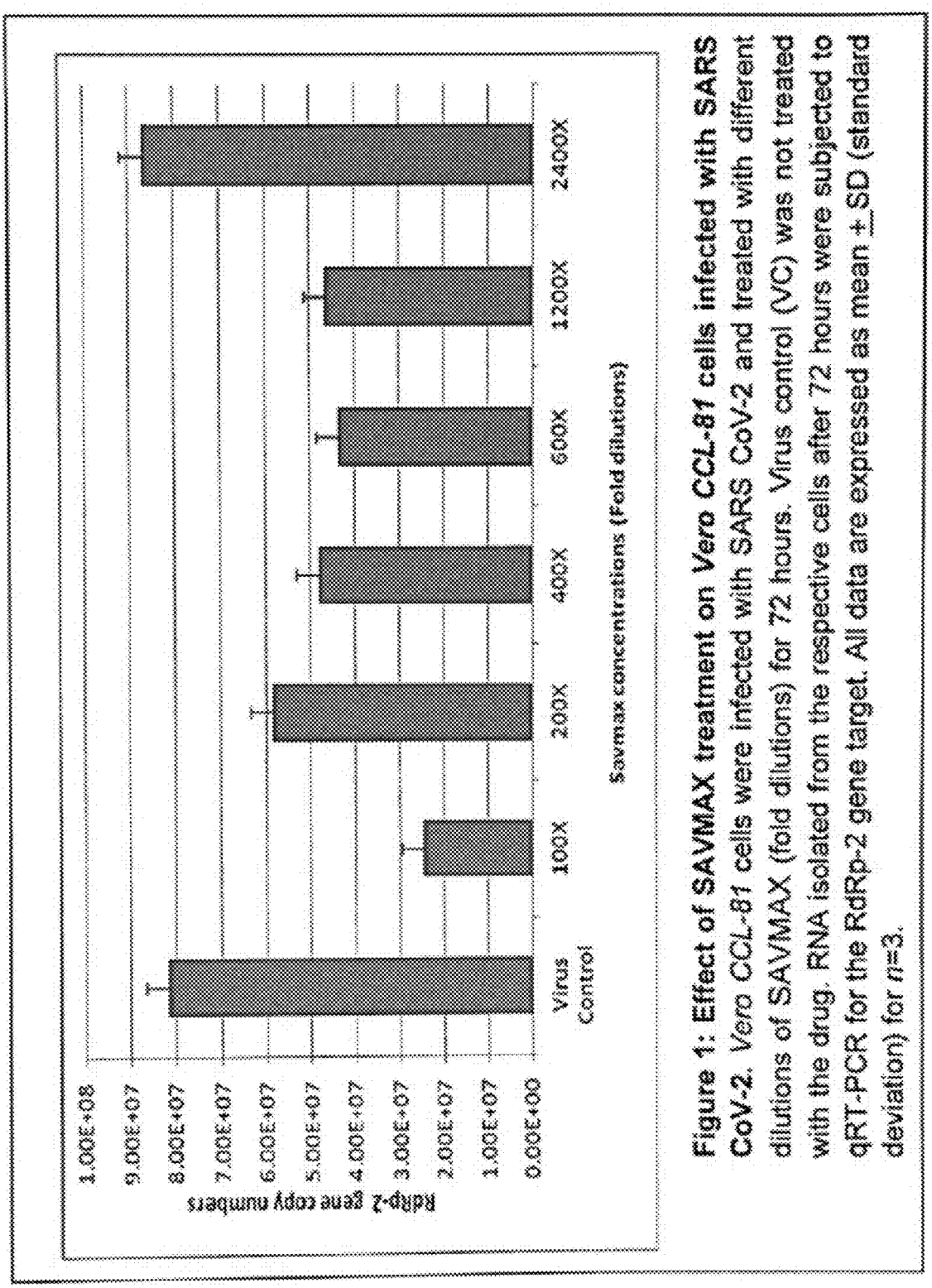
FIG. 8 shows the effect of compound of Formula II treatment on Vero CCL-81 cells infected with SARS CoV-2.
Figure 9:
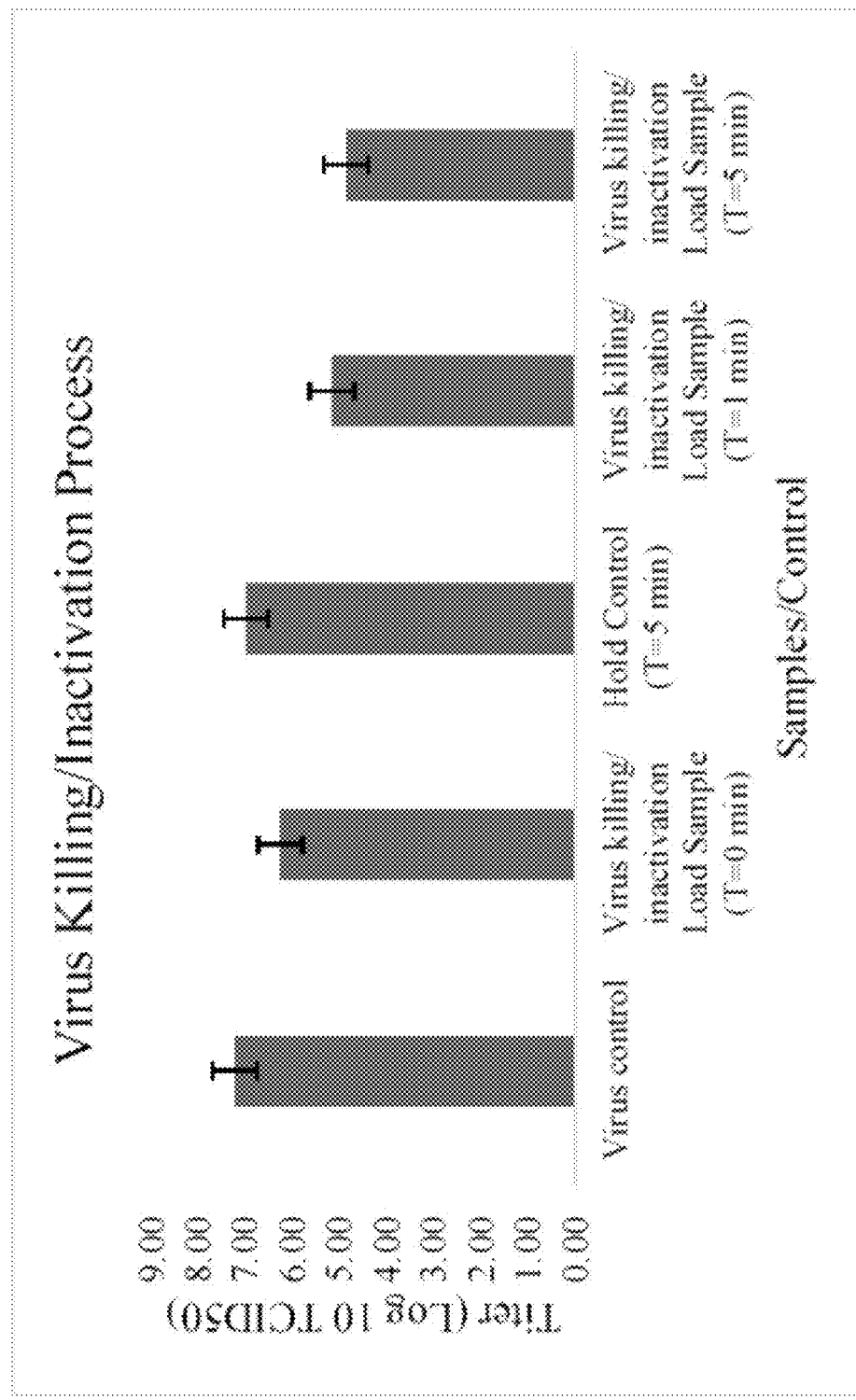
FIG. 9 illustrates the PI-3 removal efficiency of compound of Formula II.

FIG. 8 shows the effect of Formula II treatment on Vero CCL-81 cells infected with SARS CoV-2. The data is expressed as mean±SD (standard deviation) for n=3.

Activity of compound of Formula II was tested against SARS CoV-2 NIV2020-770 isolate.

Vero CCL-81 cells were infected with SARS coV-2 and treated with different dilutions of Formula II (fold dilutions) for 72 hours. Virus control (VC) was not treated with the compound of Formula II. RNA isolated from the respective cells after 72 hours were subjected to qRT-PCR for the RdRp-2 gene target.

From FIG. 8, it can be observed that the compound of formula II showed:
1. Dose dependent cytotoxicity in Vero CCL-81 cells during the anti-viral assay at the tested fold dilutions (100 fold to 2400-fold dilutions). Its $CC_{50}$ is 600-fold dilution.
2. From 100 to 600-fold dilution the anti-viral activity observed as reduction of the RDRp-2 gene is primarily due to cytotoxicity of the compound.
3. The compound shows inhibition of the RdRp-2 gene at 1200-fold dilution (~40%).

E. Activity Against Parainfluenza Virus (PI-3)

Viral clearance study (virucidal efficacy) Results.

Virus killing ability of compound of Formula II was evaluated under following process conditions.

Temperature of operation step: 23±2° C.
Starting material: 1 ml
Contact time (min): 1 minute and 5 minutes)
Virus studied: PI-3 virus (enveloped virus)
Virus spike: 10%
Mode of sample testing: Infectivity assay
Number of runs: 1

An appropriate amount compound of Formula II was taken in a 15 mL tube and spiked with 10% (v/v) of PI-3 virus stock solution and shook well for proper mixing of the virus into the product. Sample pH was confirmed to 7.0 by using pH paper, filtered using 0.22 μm filter. A portion of the sample was collected and tested immediately. The remaining sample was aliquoted (~0.5 ml×2) and stored as backups at −80+5° C. This was represented as "viral killing/inactivation Load sample (0 min)".

~500 ml of virus stock solution (PI-3) was taken in a 15 mL tube and incubated for the duration of viral killing/inactivation process step (5 min) at room temperature. 4500 μL of media containing MEM with 2% FBS was added to the respective tube to make 5 mL of virus stock solution after the incubation time. Sample of pH was confirmed to 7.0 by using pH paper, filtered using 0.22 μm filter. A portion of the sample was collected and tested immediately. The remaining sample was aliquoted (−0.5 ml×2) and stored as backups at −80±5° C. This was represented as "Viral killing/inactivation Hold Control (5 min)".

~1 mL of virus stock solution (PI-3) was taken in a 15 mL tube and added 9 mL of compound of Formula II to the virus stock solution. Shook vigorously for maximum mixing of the virus into the product and incubated for a duration of the killing/inactivation process step (5 min) at room temperature. ~4 mL of sample was collected from the incubated tube at time points of 1 minute and 5 minutes for sample analysis. Samples pH was confirmed to 7.0 using pH paper, filtered using 0.22 μm filter. A portion of the sample was collected and tested immediately. The remaining sample was aliquoted (~0.5 ml×2) and stored as backups at ~80±5° C. This was represented as "Viral killing/inactivation sample (5 Min)".

The following samples were tested for the presence of PI-3 (TCID50 Assay) as per VTF procedures by infectivity assays.

Summary of Samples:

| Sample Number | Sample |
|---|---|
| SN: 001 | Viral killing/inactivation Load Sample (0 minute) |
| SN: 002 | Hold control (5 minutes) |
| SN: 003 | Viral killing/inactivation sample (T = 1) |
| SN: 004 | Viral killing/inactivation sample (T = 5) |
| SN: 005 | Virus control |
| — | Media/negative Control |

The titration plates were incubated in CO2 incubator and observed on 7th day for TCID50 assay. The virus titre was calculated by using Reed and munch formula as per VTF procedures.

Controls for Viral Removal/Inactivation Study.

a. Stock Virus Control:

An aliquot of the sonicated and filtered (0.22 μm) stock virus (PI-3) solutions used for killing/inactivation step was tested within the assay run. These controls were determining the starting titer of the stock virus solution used for killing/inactivation purpose.

b. Negative Controls

Serum-free medium (MEM for PI-3) was served as negative control.

Quantification of Infectious Virus By Plaque Assay And $TCID_{50}$ Assay

A portion of each test and control sample was diluted in respective incomplete medium (MEM) to the end point (undiluted [at non-interference dilution if required], $10^{-1}$, $10^{-2}$, $10^{-3}$, $10^{-4}$, $10^{-5}$, $10^{-6}$, $10^{-7}$, $10^{-8}$, $10^{-9}$ and $10^{-10}$) for $TCID_{50}$ assay. The remaining material was reserved as backups at −80±5° C. Each appropriate dilution was assayed by general titration assay procedure.

Calculation of Reduction Factors in Studies to Determine Viral Clearance

The Virus reduction factor for each of the removal steps was calculated using the following formula:

$$RF=\log[(C1\times V1)/(C2\times V2)]$$

RF: Reduction Factor
C1: Concentration of virus in the starting material
V1: Volume of the starting material
C2: Concentration of virus in the post processing material
V2: Volume of the post processing material The reduction factor for the process step represents the logarithm of the ratio of the virus load at the beginning of the first process clearance step and at the end of the process clearance step. Reduction factor is normally expressed on a logarithmic scale and given in the following Tables.

The following Tables 3 and 4 provide antiviral efficacy report of the edible micelle substance of compound of Formula II on enveloped virus Bovine parainfluenza virus. FIG. 9 discloses the PI-3 removal efficiency of compound of Formula II.

TABLE 3

Viral Removal/inactivation step: PI-3 Log Reduction Value calculation

| Sample No. | Virus Titer (Log10 TCID50/mL) | Virus Titer (TCID50/mL) | pH Adjust | Dilution adjust | Volume adjust (mL) | Adjusted Titer (TCID50) | Log10 Adjusted Titer (TCID50) | 95% Conf. of titer | Log10 Reduction | 95% Conf. of Log 10 Reduction |
|---|---|---|---|---|---|---|---|---|---|---|
| SN: 005 | 7.23 | 16982436.52 | 1.00 | 1.00 | 1.0 | 1.70E+07 | 7.23 | 0.49 | NA | NA |
| SN: 001 | 2.50 | 316.23 | 1.00 | 600 | 10.0 | 1.90E+06 | 6.28 | 0.25 | ND | ND |
| SN: 002 | 6.00 | 1000000.00 | 1.00 | 1.00 | 10.0 | 1.00E+07 | 7.00 | 0.51 | ND | ND |
| SN: 003 | NA | *2.50 | 1.00 | 6000 | 10.0 | 1.50E+05 | 5.18 | NA | ND | ND |
| SN: 004 | NA | **1.25 | 1.00 | 6000 | 10.0 | 7.50E+04 | 4.88 | NA | 2.12 | 0.51 |

SN: 001: Virus killing/inactivation Load Sample (T = 0 min)
SN: 002: Hold Control (T = 5 min)
SN: 003: Virus killing/inactivation Sample (T = 1 min)
SN: 004: Virus killing/inactivation Sample (T = 5 min)
SN: 005: Virus control
NA: Not applicable
ND: Not done
*2.5 value denotes 2 wells was positive for virus out of 8 wells tested.
2 well positive/0.8 mL of 8 wells
2/0.8 = 2.5
**1.25 value denotes 1 wells was positive for virus out of 8 wells tested.
1 well positive/0.8 mL of 8 wells
1/0.8 = 1.25
E denotes exponent.

TABLE 4

Overall Log$_{10}$ Reduction of PI3 virus in 5 minutes (enveloped virus)

| Process Step | Virus | Sample description | Sample No. | Log$_{10}$ Reduction | % Log reduction |
|---|---|---|---|---|---|
| viral killing/ inactivation | PI-3 | Viral killing/ inactivation T = 5 min | SN: 004 | 2.12 | 99.25 |

The above results show that compound of Formula II has high anti-viral property.

F. Antimicrobial Activity

Compound of Formula II was tested for antimicrobial activity by the following protocols.

Name of Test:—Evaluation of Antimicrobial Activity

Organism Used.
1. *Escherichia coli* (ATCC 8739)
2. *Staphylococcus aureus* (ATCC 6538)
3. *Bacillus subtilis* (ATCC 6633)

Test Condition:

Contact time: 30 seconds, 1 Minute, 5 Minute and 10 Minutes,

Sample concentration: 10 mg/10 ml

Incubation temperature: 34° C., 25° C.

Neutralizer used: Dey engley neutralizing broth

TABLE 5

Result: Initial Bactericidal, fungicidal and Sporocidal activity.

| Sr. No. | Organism used | Inoculum strength Cfu/ml |
|---|---|---|
| 1 | *Escherichia coli* (ATCC 8739) | 70000000 |
| 2 | *Staphylococcus aureus* (ATCC 6538) | 74000000 |
| 3 | *Bacillus subtilis* (ATCC 6633) | 76000000 |

TABLE 6

Percentage reduction of the organisms after 30 seconds, 1 minute, 5 minutes, 10 minutes and 20 minutes.

| Organism used | Initial Inoculum strength Cfu/ml | % reduction after 30 seconds | % reduction after 1 minute | % reduction after 5 minutes | % reduction after 10 minutes | % reduction after 20 minutes |
|---|---|---|---|---|---|---|
| *Escherichia coli* (ATCC 8739) | 70000000 | 31.42857 | 55.71429 | 60.00000 | 64.28571 | 99.9851 |
| *Staphylococcus aureus* (ATCC 6538) | 74000000 | 31.08108 | 43.24324 | 54.05405 | 62.16216 | 99.9627 |
| *Bacillus subtilis* (ATCC 6633) | 76000000 | 27.63158 | 44.73684 | 59.21053 | 65.78947 | 99.9789 |

From above table, it can be understood that the compound of the present invention has excellent antimicrobial activity.

G. Activity Against Avian Influenza

Compound of Formula II was tested on poultry birds infected with avian influenza, the mortality rate observed was at 550 per day in 14000 flocks. The therapeutic effect of compound of Formula II was profound that is 92% reduction in mortality of avian influenza infected birds was observed after treatment with compound of Formula II at 30 ml per 100 birds once daily. The effect suggests the therapeutic antiviral efficacy of the molecule.

Table 7: Reduction in Mortality of Birds Infected with Avian Influenza

92% reduction in avian influenza mortality was observed when compound of Formula II was given to the birds infected with avian influenza.

Compound of Formula II was diluted in water (1:9) and was given at 30 ml per 100 birds per day.

TABLE 7

| Number of days | Mortality |
|---|---|
| Day 0 | 550 (compound of Formula II was not given) |
| Day 1 | 526 |
| Day 2 | 514 |
| Day 3 | 533 |
| Day 4 | 553 |
| Day 5 | 415 |
| Day 6 | 315 |
| Day 7 | 192 |
| Day 8 | 148 |
| Day 9 | 97 |
| Day 10 | 78 |
| Day 11 | 45 |
| Day 12 | 52 |

H. $^1$H-$^1$H Correlation Spectroscopy (COSY)

FIG. 10 (FIGS. 10A, 10B, 10C and 10D) is $^1$H-$^1$H Correlation Spectroscopy (COSY) results of compound of Formula II.

Figure 10A:
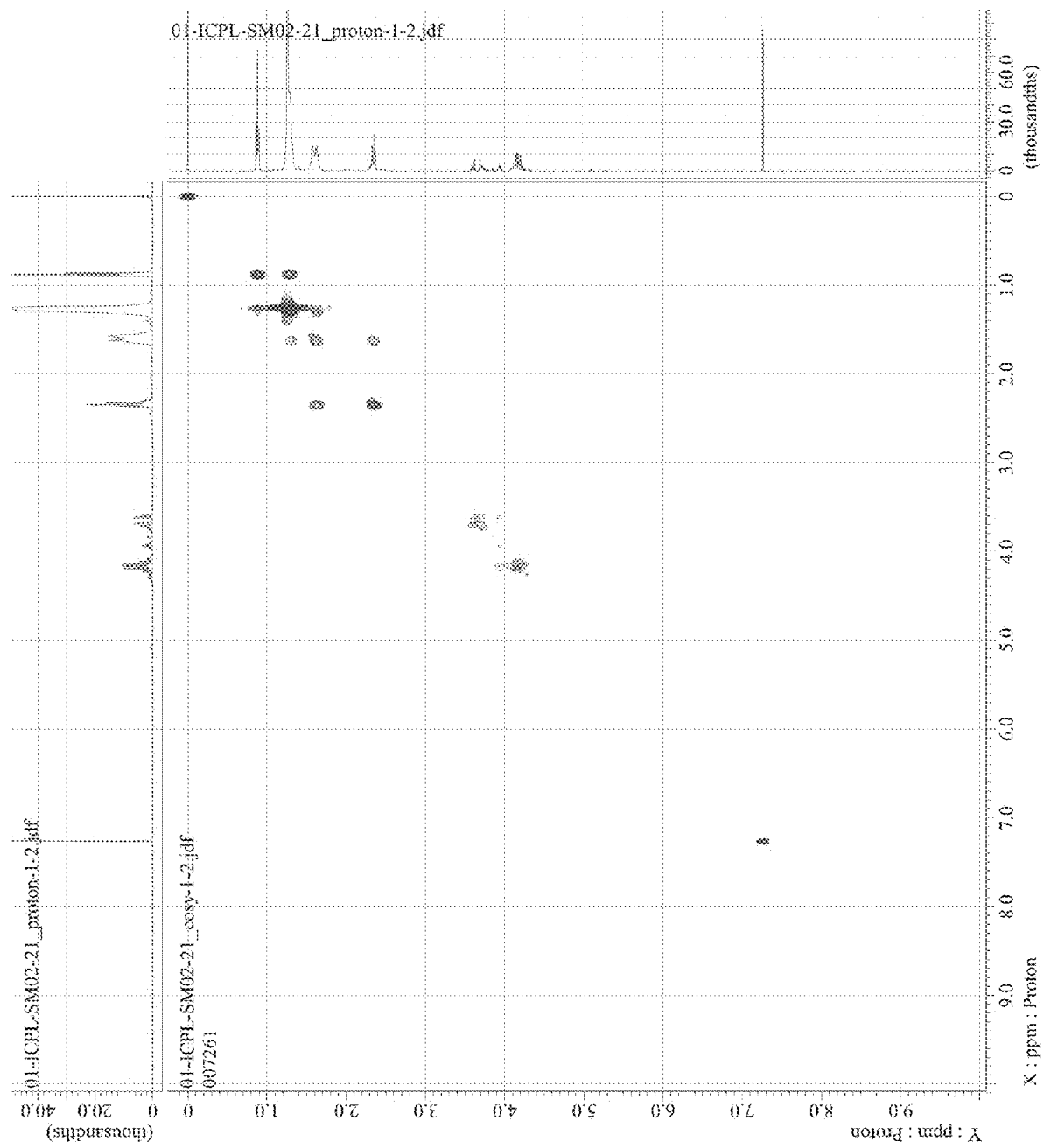
FIG. 10 (FIGS. 10A, 10B, 10C and 10D) illustrates $^1$H-$^1$H Correlation Spectroscopy (COSY) results of compound of Formula II.
Figure 10B:
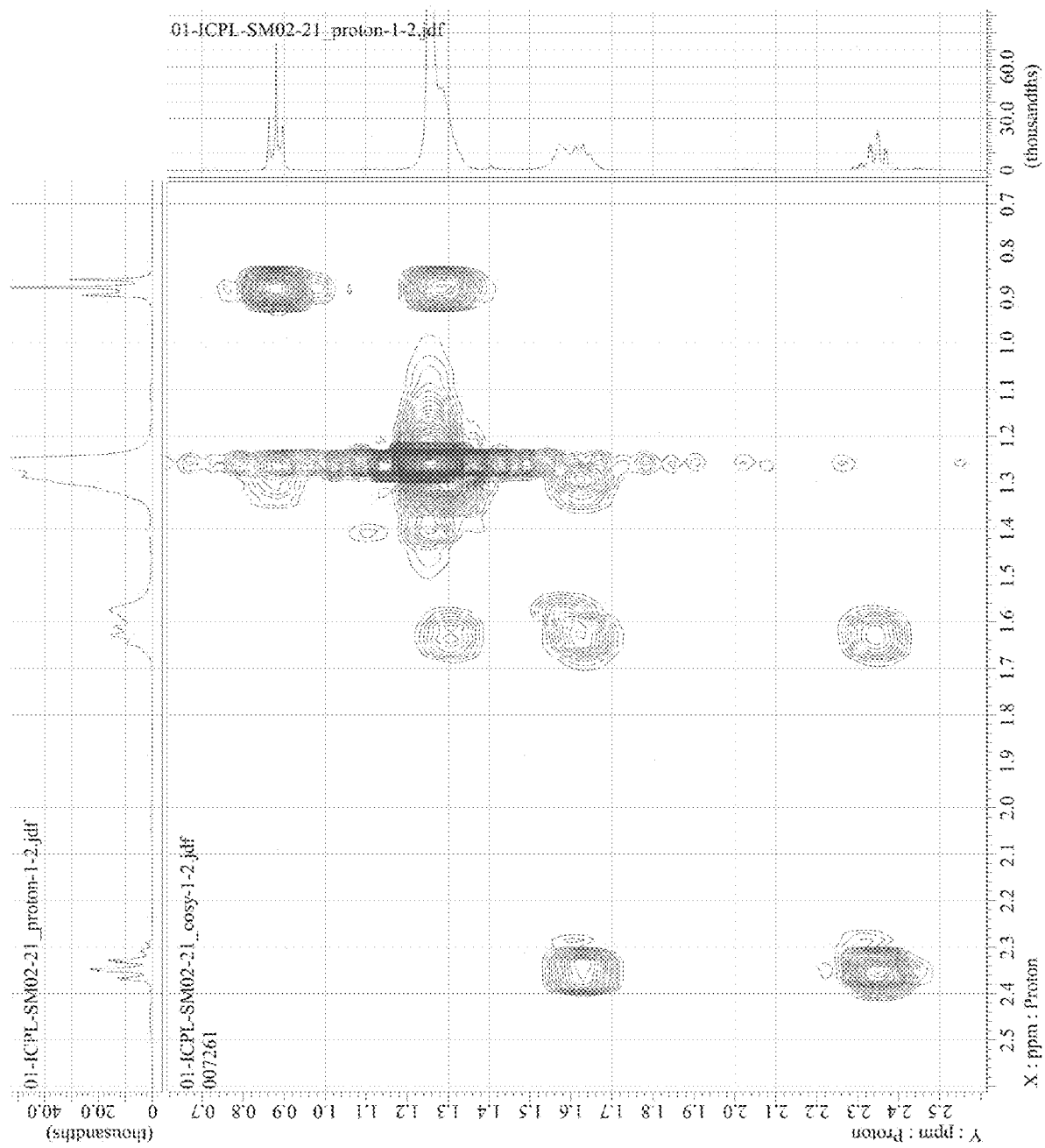

| Processing Parameters for FIGS. 10A and 10B: | |
|---|---|
| sexp( 0.3[Hz], 0.0[s] ) | Instrument - NMR-500 MHz(JEOL) |
| trapezoid( 0[%], 0[%], 80[%], 100[%] ) | Instrument id - NMR-02 |
| zerofill( 4 ) | Solvent = CHLOROFORM-D |
| fft( 1, TRUE, TRUE ) | Spectrometer = JNM-ECZ400S/L1 |
| machinephase | Experiment = cosy.jxp |
| ppm | Acquisition Parameter |
| auto_reference( 5[%], TRUE ) | X_Domain = Proton |
| phase( −2.08491, −4.78679, 50[%] ) | X_Offset = 5[ppm] |
| | X_Sweep = 7.51201923[kHz] |
| | Scans = 8 |
| | Relaxation_Delay = 1.5[s] |

Figure 10C:
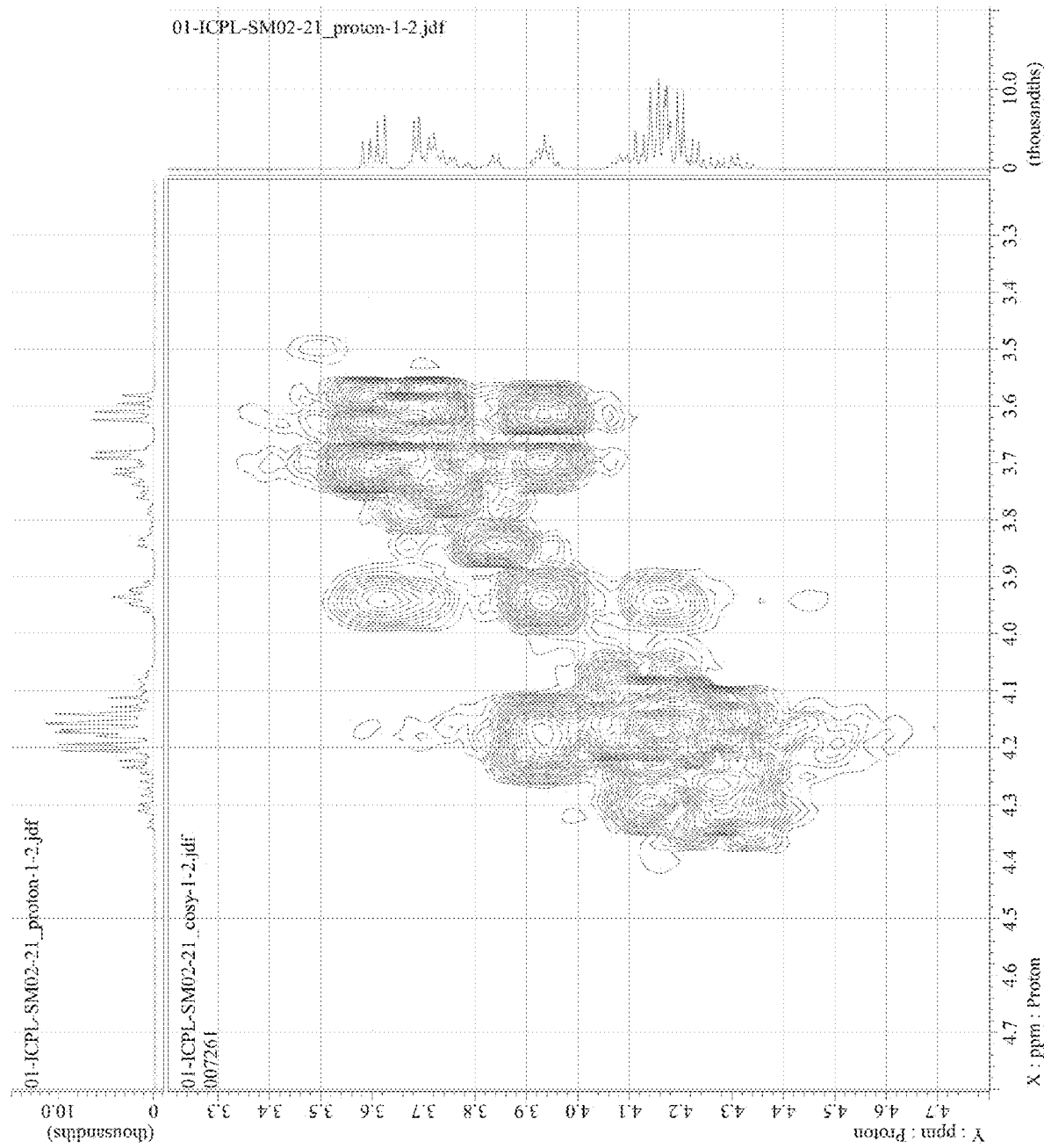
Figure 10D:
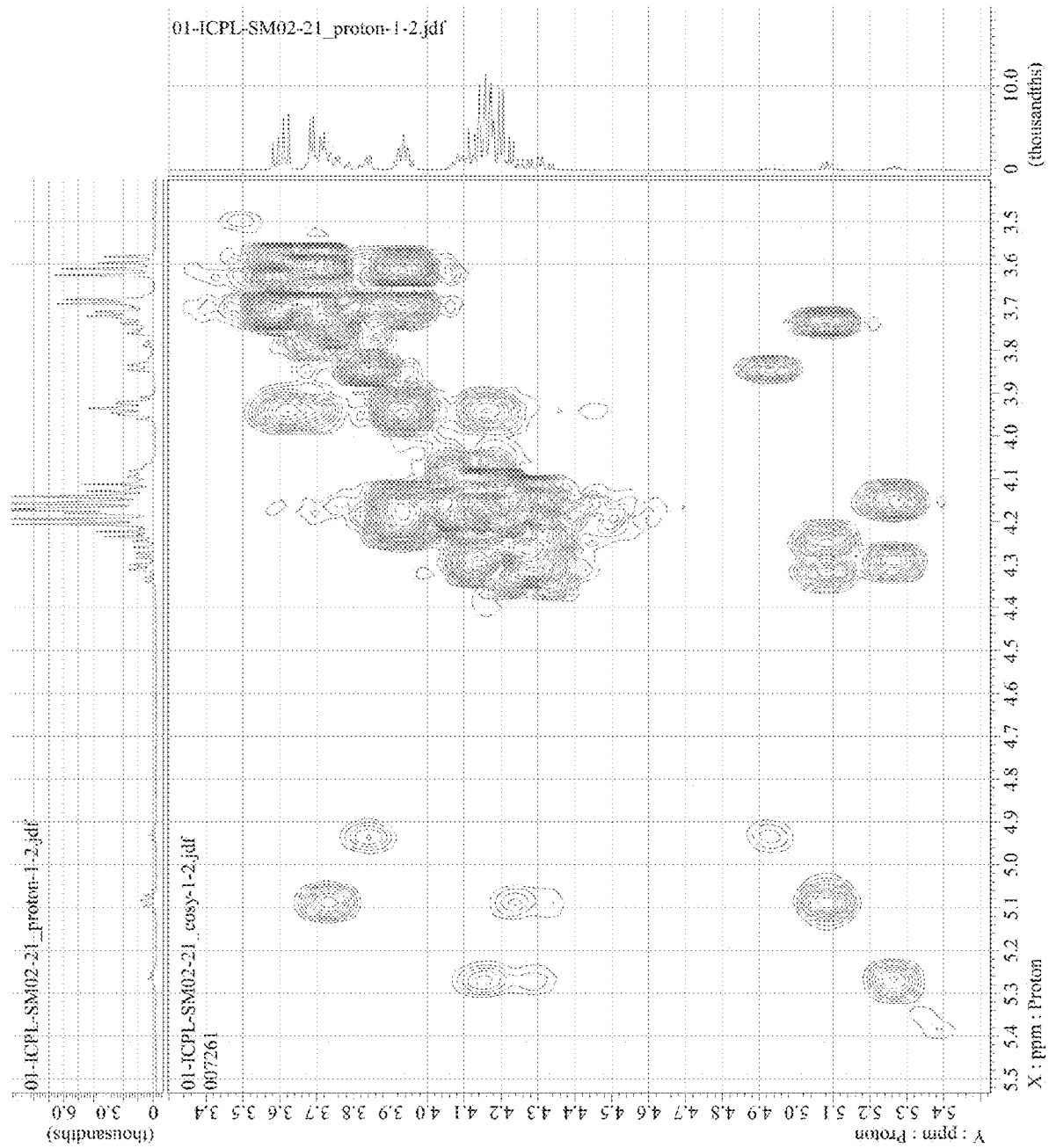

| Processing Parameters for FIGS. 10C and 10D: | |
|---|---|
| sinbell_auto | Instrument - NMR-500 MHz(JEOL) |
| fft( 1, TRUE, TRUE ) | Instrument id - NMR-02 |
| ppm | Solvent = CHLOROFORM-D |
| [transpose] | Spectrometer = JNM-ECZ400S/L1 |
| sinbell_auto | Experiment = cosy.jxp |
| zerofill( 4 ) | Acquisition Parameter |
| fft( 1, TRUE, TRUE ) | X_Domain = Proton |
| ppm | X_Offset = 5[ppm] |
| abs | X_Sweep = 7.51201923[kHz] |
| [transpose] | Scans = 8 |
| | Relaxation_Delay = 1.5[s] |

I. CHNS Analysis

Figure 11:
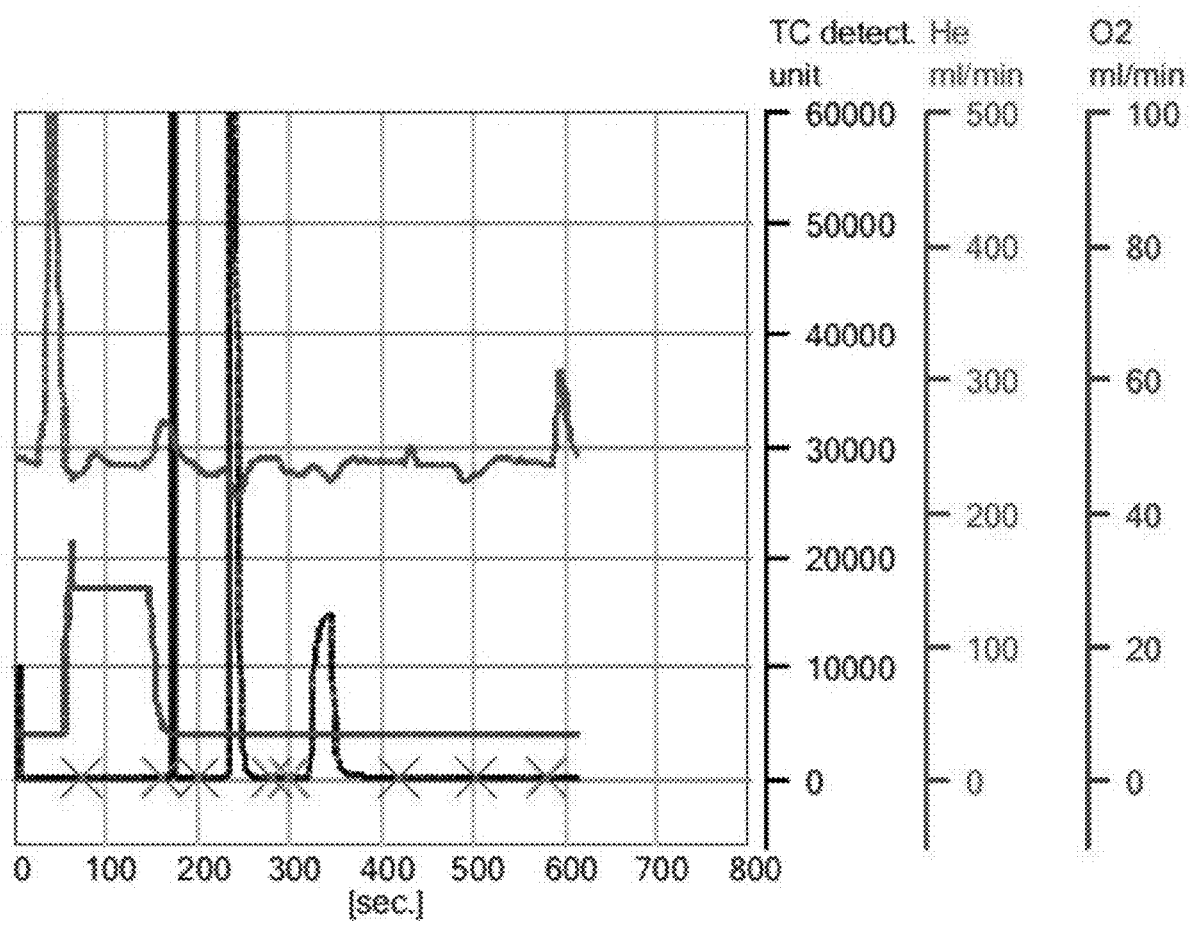
FIG. 11 illustrates the graphic report of CHNS analysis of compound of Formula II.

FIG. 11 is the graphic report of CHNS analysis of compound of Formula II.

The following results were obtained in CHNS analysis:

TABLE 8

| Results of CHNS Analysis | | | | | |
|---|---|---|---|---|---|
| Weight of the sample | Method | Nitrogen (N) [%] | Carbon (C) [%] | Hydrogen (H) [%] | Sulphur (S) [%] |
| 3.8860 | 5 mg 90 s | 0.00 | 66.94 | 11.344 | 0.00 |

The foregoing description of the invention has been set merely to illustrate the invention and is not intended to be limiting. Since modifications of the disclosed embodiments incorporating the spirit and substance of the invention may occur to person skilled in the art, the invention should be construed to include everything within the scope of the disclosure.

The invention claimed is:

1. A compound of Formula A

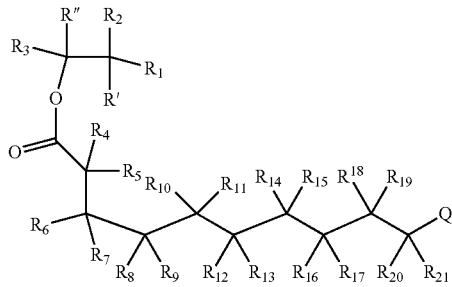

Formula A wherein R' and R'' each independently is selected from —H, —OH, alkyl, hydrocarbylalkyl, alkenyl, alkynyl, phenyl, haloalkanes, fluoroalkane, chloroalkane, bromoalkane, iodoalkane, carbonylaldehyde, haloformylcarbonateester, carboxylatecarboxyl, carboalkoxy, hydroperoxy, peroxy, ether, hemiacetal, hemiketal, acetal, ketal, orthoester, methylenedioxyorthocarbonate ester, carboxylic anhydride, carboxamide, primary amine, tertiary amine, 40 ammonium ion, primary ketimine, secondary ketimine, imineimide, azidazo, cyanate, nitrate, nitrilenitrite, nitro, oxime, pyridyl, carbamate, thiol, sulfide, disulfide, sulfinyl, sulfonyl, sulfino, sulfo, thiocyanate, isothiocyanate, carbonothioyl, thioster, provided that R' is —OH, when R'' is —H, alkyl, hydrocarbylalkyl, alkenyl, alkynyl, phenyl, haloalkanes, fluoroalkane, chloroalkane, bromoalkane, iodoalkane, carbonylaldehyde, haloformylcarbonateester, carboxylatecarboxyl, carboalkoxy, hydroperoxy, peroxy, ether, hemiacetal, hemiketal, acetal, ketal, orthoester, methylenedioxyorthocarbonate ester, carboxylic anhydride, carboxamide, primary amine, tertiary amine, 40 ammonium ion, primary ketimine, secondary ketimine, imineimide, azidazo, cyanate, nitrate, nitrilenitrite, nitro, oxime, pyridyl, carbamate, thiol, sulfide, disulfide, sulfinyl, sulfonyl, sulfino, sulfo, thiocyanate, isothiocyanate, carbonothioyl, thioster;

or

R'' is —OH, when R' is —H, alkyl, hydrocarbylalkyl, alkenyl, alkynyl, phenyl, haloalkanes, fluoroalkane, chloroalkane, bromoalkane, iodoalkane, carbonylaldehyde, haloformylcarbonateester, carboxylatecarboxyl, carboalkoxy, hydroperoxy, peroxy, ether, hemiacetal, hemiketal, acetal, ketal, orthoester, methylenedioxyorthocarbonate ester, carboxylic anhydride, carboxamide, primary amine, tertiary amine, 40 ammonium ion, primary ketimine, secondary ketimine, imineimide, azidazo, cyanate, nitrate, nitrilenitrite, nitro, oxime, pyridyl, carbamate, thiol, sulfide, disulfide, sulfinyl, sulfonyl, sulfino, sulfo, thiocyanate, isothiocyanate, carbonothioyl, thioster;

$R_1$-$R_{21}$ each independently is selected from —H or alkyl;

Q is selected from —$CH_3$,

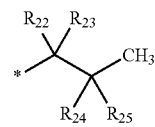

-continued
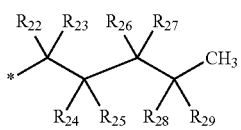
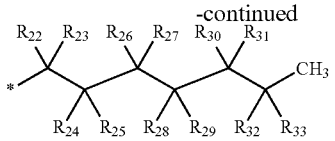
wherein * represents point of attachment and $R_{22}$-$R_{33}$ each independently is selected from —H or alkyl.
2. The compound as claimed in claim 1 represented by the structures of Formula I, Formula I-A, Formula I-B, Formula I-C, Formula I-D, Formula I-E, Formula I-F, Formula I-G:
Formula I
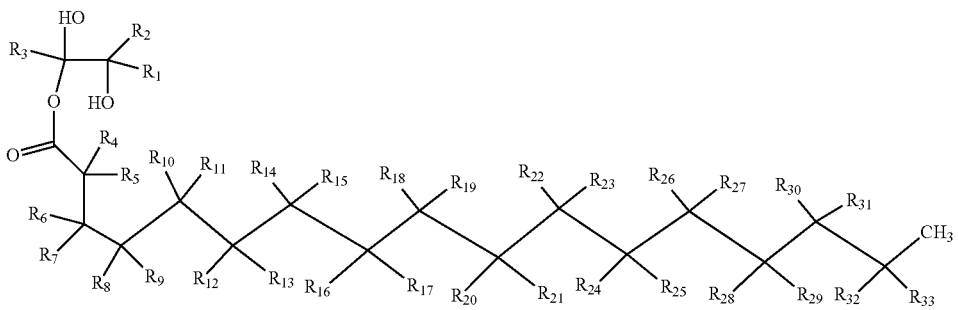
Formula I-A
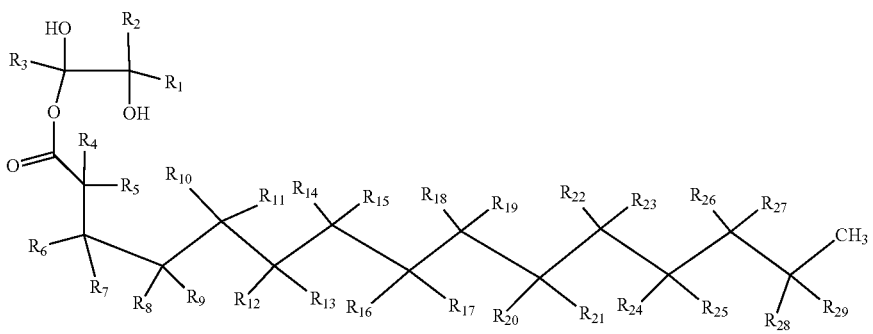
Formula I-B
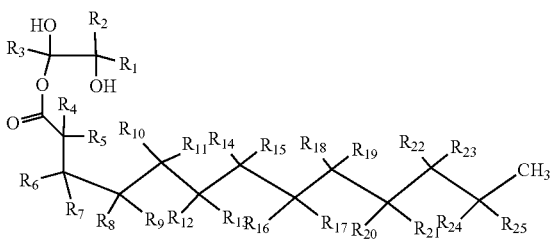
Formula I-C
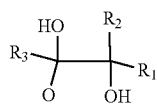
Formula I-D
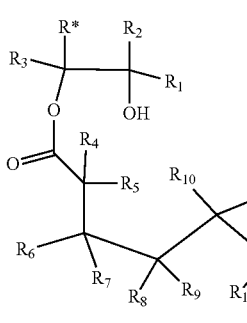

-continued

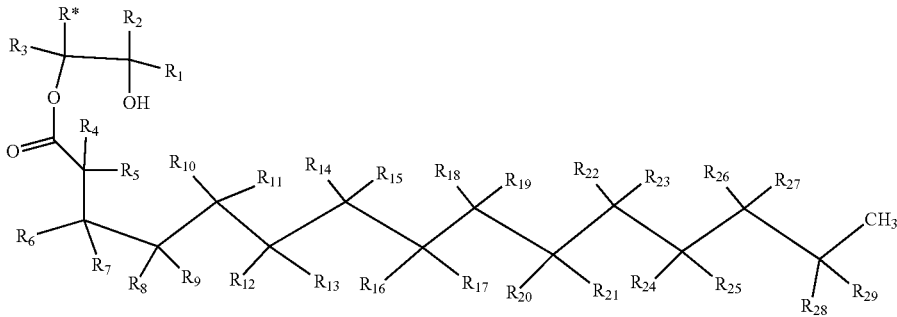

Formula I-E

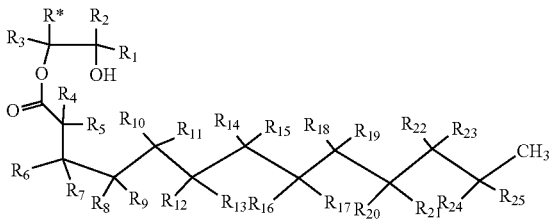

Formula I-F

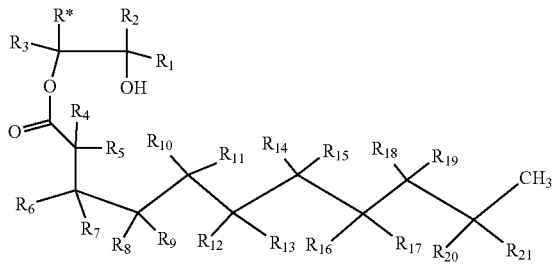

Formula I-G wherein, $R_1$-$R_{33}$ each independently is selected from —H or alkyl; and R" is —H, alkyl, hydrocarbylalkyl, alkenyl, alkynyl, phenyl, haloalkanes, fluoroalkane, chloroalkane, bromoalkane, iodoalkane, carbonylaldehyde, haloformylcarbonateester, carboxylatecarboxyl, carboalkoxy, hydroperoxy, peroxy, ether, hemiacetal, hemiketal, acetal, ketal, orthoester, methylenedioxyorthocarbonate ester, carboxylic anhydride, carboxamide, primary amine, tertiary amine, 40 ammonium ion, primary ketimine, secondary ketimine, imineimide, azidazo, cyanate, nitrate, nitrilenitrite, nitro, oxime, pyridyl, carbamate, thiol, sulfide, disulfide, sulfinyl, sulfonyl, sulfino, sulfo, thiocyanate, isothiocyanate, carbonothioyl, thioester.

3. The compound as claimed in claim 2 represented by compound of Formula I

Formula I

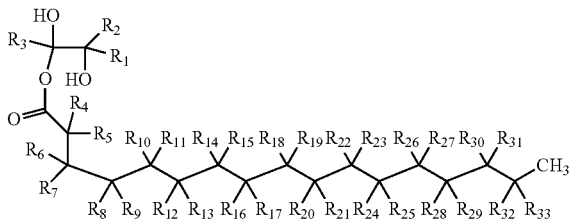

wherein $R_1$-$R_{33}$ each independently is selected from —H or alkyl.

4. The compound as claimed in claim 1, wherein the compound of Formula A comprises a single —OH group.

5. The compound as claimed in claim 1 comprising $C_{10}$-$C_{25}$ long aliphatic chains, wherein the long aliphatic chains consist of carbon hydrogen and oxygen.

6. The compound as claimed in claim 3 having the structure as Formula II, (1,2-dihydroxy ethyl heptadecanoate)

Formula II

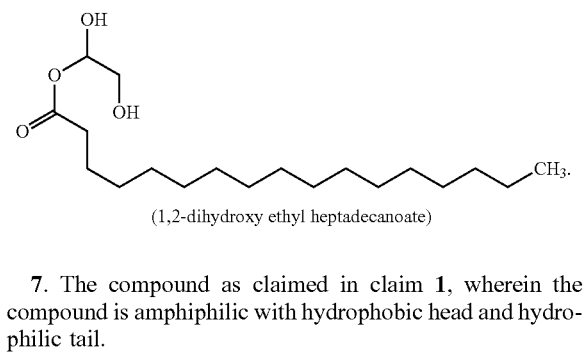

(1,2-dihydroxy ethyl heptadecanoate)

7. The compound as claimed in claim 1, wherein the compound is amphiphilic with hydrophobic head and hydrophilic tail.

8. The compound as claimed in claim 1, wherein the macromolecular structure of compound is micelle or reverse micelle.

9. A method of preparation of compound of Formula A as claimed in claim 1, the method comprising the steps of:
 a. mixing an ester in an alcohol with application of heat to obtain an ester-alcohol solution; and
 b. adding water to the ester-alcohol solution with vigorous stirring to obtain compound of Formula A.

10. The method as claimed in claim 9, wherein compound of Formula A is obtained as a semi liquid or semi solid pasty substance and wherein the density of the compound largely depends on the quantity of water added either during synthesis or after synthesis.

11. The method as claimed in claim 9, wherein residual precursor reagents (ester or alcohol) is present or absent along with compound of Formula A.

12. The method as claimed in claim 9, wherein the ester is selected from one or more of glycerol monostearate, glycerol monolaurate, glycerol monooleate, glycerin fatty acid esters, acetic acid esters of monoglycerides, lactic acid esters of monoglycerides, citric acid esters of monoglycerides, succinic acid esters of monoglycerides, diacetyl tartaric acid esters of monoglycerides, polyglycerol esters of fatty acids, polyglycerol polyricinoleate, sorbitan esters of fatty acids, propylene glycol esters of fatty acids, sucrose esters of fatty acids, calcium stearoyl di lactate, lecithin, enzyme digested lecithin/enzyme treated lecithin, 2-arachidonoylglycerol, ascorbyl palmitate, ascorbyl stearate, cetylmyristoleate, cetyl palmitate, di-deuterated linoleic acid ethyl ester, diglyceride, ethyl decadienoate, ethyl decanoate, ethyl eicosapentaenoic acid, ethyl macadamiate, ethylhexyl palmitate, fatty acid methyl ester, glyceryl hydroxystearate, glycol distearate, isopropyl jojobate, methyl ricinoleate, mono- and diglycerides of fatty acids, monoctanoin, monoglyceride, monolaurin 2-oleoylglycerol, omega-3 acid ethyl esters, polyglycerol, polyricinoleate, sorbitan monooleate, sorbitan monopalmitate, virodhamine.

13. The method as claimed in claim 9, wherein the ester is selected from one or more of allyl hexanoate, benzyl acetate, bornyl acetate, butyl acetate, butyl butyrate, butyl propanoate, ethyl acetate, ethyl benzoate, ethyl butyrate, ethyl hexanoate, ethyl cinnamate, ethyl ethanoate, ethyl formate, ethyl heptanoate, ethyl isovalerate, ethyl lactate, ethyl nonanoate, ethyl pentanoate, geranyl acetate, geranyl butyrate, geranyl pentanoate, isobutyl acetate, isobutyl formate, isoamyl acetate, isopropyl acetate, linalyl acetate, linalyl butyrate, linalyl formate, methyl acetate, methyl anthranilate, methyl benzoate, methyl butyrate (methyl butanoate), methyl cinnamate, methyl pentanoate (methyl valerate), methyl phenylacetate, methyl salicylate (oil of wintergreen), nonyl caprylate, octyl acetate, octyl butyrate, amyl acetate (pentyl acetate), pentyl butyrate (amyl butyrate), pentyl hexanoate (amyl caproate), pentyl pentanoate (amyl valerate), propyl acetate, propyl hexanoate, propyl isobutyrate, terpenyl butyrate.

14. The method as claimed in claim 10, wherein the ester is selected from glycerol monostearate, glycerol monooleate and glycerol monolaurate.

15. The method as claimed in claim 9, wherein the alcohol is selected from methanol, ethanol, propanol and butanol or combinations thereof.

16. The method as claimed in claim 9, wherein the water is distilled water.

17. The method as claimed in claim 9, the method comprising the steps of:

a. mixing glycerol monostearate in ethanol in a ratio of 20:5 w/v, with application of heat at a temperature of 40° C. to 200° C. to obtain a glycerol monostearate-ethanol solution; and b. adding distilled water in the glycerol monostearate-ethanol solution in a ratio of 20:5:75 w/v/v (glycerol monostearate: ethanol: water) with vigorous stirring to obtain a pasty semi liquid substance of Formula II.

18. The method as claimed in claim 9 comprising carrying out the reaction in the absence of a catalyst, wherein the reaction between the ester and alcohol is a hydrolysis reaction and takes place by a sudden change in physical condition of ester after dissolving in alcohol under heating, the reaction allows the water molecules to initiate hydrolysis of the ester molecules by breaking bonds resulting in compound of Formula A, Formula I to I-G or Formula II having hydrophilic property.

19. A pharmaceutical composition comprising one or more compounds covered by Formula A as claimed in claim 1 with one or more pharmaceutically acceptable excipient in the presence or absence of one or more active agent selected from antiviral and antimicrobial compounds.

20. A stable colloidal solution comprising one or more compound covered by Formula A as claimed in claim 1 and water.

21. A method of treatment of infection caused by virus or microbes by administering one or more compounds covered by Formula A as claimed in claim 1, wherein the virus is selected from any virus or enveloped virus or SARS COV 2 virus, parainfluenza virus, paramyxoviruses, Hendra virus (HeV) and Nipah virus (NiV), avian influenza virus, Newcastle disease/Ranikhet disease virus.

22. A method of inhibition of a virus, the method comprising directly killing the virus by disrupting the lipid layer of the envelope of the virus by administering one or more compounds or composition or colloidal solution of compound of Formula A as claimed in claim 1.

23. The method as claimed in claim 21, wherein the protein of the viral envelop is disintegrated.

24. The method as claimed in claim 21, wherein the RNA of the virus is disintegrated.

* * * * *